(12) United States Patent
Truckai et al.

(10) Patent No.: US 7,186,253 B2
(45) Date of Patent: *Mar. 6, 2007

(54) ELECTROSURGICAL JAW STRUCTURE FOR CONTROLLED ENERGY DELIVERY

(75) Inventors: Csaba Truckai, Saratoga, CA (US); James Baker, Palo Alto, CA (US); Bruno Strul, Portola Valley, CA (US); John H. Shadduck, Tiburon, CA (US)

(73) Assignee: SurgRx, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/118,881

(22) Filed: Apr. 29, 2005

(65) Prior Publication Data

US 2005/0192568 A1    Sep. 1, 2005

Related U.S. Application Data

(63) Continuation of application No. 10/032,867, filed on Oct. 22, 2001, now Pat. No. 6,929,644.

(51) Int. Cl.
*A61B 18/14* (2006.01)
*A61B 18/12* (2006.01)

(52) U.S. Cl. .......................... 606/49; 606/51
(58) Field of Classification Search ........... 606/49–52, 606/96, 98
See application file for complete search history.

(56) References Cited

U.S. PATENT DOCUMENTS 659,409 A    10/1900  Mosher 1,586,645 A    6/1926  Bleman
1,798,902 A    3/1931  Raney.

(Continued)

FOREIGN PATENT DOCUMENTS

EP    341 446 A2    4/1989

(Continued)

OTHER PUBLICATIONS

Corson, S.L., "Two new laparoscopic instruments: Bipolar sterilizing forceps and uterine manipulator," *Medical Instrumentation*, 11(1):7-8 (1997).

(Continued)

*Primary Examiner*—Roy D. Gibson
*Assistant Examiner*—Aaron Roane
(74) *Attorney, Agent, or Firm*—Townsend and Townsend and Crew LLP.

(57) ABSTRACT

A working end of a surgical instrument that carries first and second jaws for delivering energy to tissue. In a preferred embodiment, at least one jaw of the working end defines a tissue-engagement plane that contacts the targeted tissue. The cross-section of the engagement plane reveals that it defines a surface conductive portion that overlies a variably resistive matrix of a temperature-sensitive resistive material or a pressure-sensitive resistive material. An interior of the jaw carries a conductive material or electrode that is coupled to an Rf source and controller. In an exemplary embodiment, the variably resistive matrix can comprise a positive temperature coefficient (PTC) material, such as a ceramic, that is engineered to exhibit a dramatically increasing resistance (i.e., several orders of magnitude) above a specific temperature of the material.

10 Claims, 17 Drawing Sheets

U.S. PATENT DOCUMENTS

| | | | |
|---|---|---|---|
| 1,881,250 A | 10/1932 | Tomlinson |
| 2,031,682 A | 2/1936 | Wappler et al. |
| 3,651,811 A | 3/1972 | Hildebrandt et al. |
| 3,685,518 A | 8/1972 | Beuerle et al. |
| 3,730,188 A | 5/1973 | Ellman |
| 3,768,482 A | 10/1973 | Shaw |
| 3,826,263 A | 7/1974 | Cage et al. |
| 4,092,986 A | 6/1978 | Schneiderman |
| 4,198,957 A | 4/1980 | Cage et al. |
| 4,219,025 A | 8/1980 | Johnson |
| 4,231,371 A | 11/1980 | Lipp |
| 4,232,676 A | 11/1980 | Herczog |
| 4,271,838 A | 6/1981 | Lasner et al. |
| 4,353,371 A | 10/1982 | Cosman |
| 4,370,980 A | 2/1983 | Lottick |
| 4,375,218 A | 3/1983 | Digeronimo |
| 4,492,231 A | 1/1985 | Auth |
| 4,590,934 A | 5/1986 | Malis et al. |
| 4,608,981 A | 9/1986 | Rothfuss et al. |
| 4,633,874 A | 1/1987 | Chow et al. |
| 4,655,216 A | 4/1987 | Tischer |
| 4,671,274 A | 6/1987 | Sorochenko |
| 4,691,703 A | 9/1987 | Auth et al. |
| 4,763,669 A | 8/1988 | Jaeger |
| 4,785,807 A | 11/1988 | Blanch |
| 4,848,337 A | 7/1989 | Shaw et al. |
| 4,850,353 A | 7/1989 | Stasz et al. |
| 4,887,612 A | 12/1989 | Esser et al. |
| 4,940,468 A | 7/1990 | Petillo |
| 4,958,539 A | 9/1990 | Stasz et al. |
| 4,969,885 A | 11/1990 | Farin |
| 4,985,030 A | 1/1991 | Melzer et al. |
| 5,009,656 A | 4/1991 | Reimels |
| 5,057,106 A | 10/1991 | Kasevich et al. |
| 5,057,107 A | 10/1991 | Parins et al. |
| 5,085,659 A | 2/1992 | Rydell |
| 5,104,025 A | 4/1992 | Main et al. |
| 5,122,137 A | 6/1992 | Lennox |
| 5,147,356 A | 9/1992 | Bhatta |
| 5,147,357 A | 9/1992 | Rose et al. |
| 5,151,102 A | 9/1992 | Kamiyama et al. |
| 5,190,541 A | 3/1993 | Abele et al. |
| 5,201,900 A | 4/1993 | Nardella |
| 5,207,691 A | 5/1993 | Nardella |
| 5,258,006 A | 11/1993 | Rydell et al. |
| 5,267,998 A | 12/1993 | Hagen |
| 5,269,780 A | 12/1993 | Roos |
| 5,290,286 A | 3/1994 | Parins |
| 5,306,280 A | 4/1994 | Bregen et al. |
| 5,308,311 A | 5/1994 | Eggers et al. |
| 5,324,289 A | 6/1994 | Eggers |
| 5,336,221 A | 8/1994 | Anderson |
| 5,360,428 A | 11/1994 | Hutchinson, Jr. |
| 5,364,389 A | 11/1994 | Anderson |
| 5,389,098 A | 2/1995 | Tsuruta et al. |
| 5,403,312 A | 4/1995 | Yates et al. |
| 5,417,687 A | 5/1995 | Nardella et al. |
| 5,443,463 A | 8/1995 | Stern et al. |
| 5,445,638 A | 8/1995 | Rydell et al. |
| 5,451,224 A | 9/1995 | Goble et al. |
| 5,458,598 A | 10/1995 | Feinberg et al. |
| 5,480,397 A | 1/1996 | Eggers et al. |
| 5,480,398 A | 1/1996 | Eggers et al. |
| 5,507,106 A | 4/1996 | Fox |
| 5,531,744 A | 7/1996 | Nardella et al. |
| 5,571,153 A | 11/1996 | Wallstén |
| 5,573,535 A | 11/1996 | Viklund |
| 5,593,406 A | 1/1997 | Eggers et al. |
| 5,611,798 A | 3/1997 | Eggers et al. |
| 5,624,452 A | 4/1997 | Yates et al. |
| 5,674,220 A | 10/1997 | Fox et al. |
| 5,693,051 A | 12/1997 | Schulze et al. |
| 5,716,366 A | 2/1998 | Yates |
| 5,735,848 A | 4/1998 | Yates et al. |
| 5,755,717 A | 5/1998 | Yates et al. |
| 5,766,166 A | 6/1998 | Hooven |
| 5,776,130 A | 7/1998 | Buysse et al. |
| 5,797,938 A | 8/1998 | Paraschal et al. |
| 5,800,449 A | 9/1998 | Wales |
| 5,807,392 A | 9/1998 | Eggers et al. |
| 5,833,690 A | 11/1998 | Yates et al. |
| 5,891,142 A * | 4/1999 | Eggers et al. ................ 606/51 |
| 5,911,719 A | 6/1999 | Eggers |
| 5,947,984 A | 9/1999 | Whipple |
| 6,019,758 A | 2/2000 | Slater |
| 6,039,733 A | 3/2000 | Buysse et al. |
| 6,074,389 A | 6/2000 | Levine et al. |
| 6,086,586 A | 7/2000 | Hooven et al. |
| 6,113,598 A | 9/2000 | Baker |
| 6,139,508 A | 10/2000 | Simpson et al. |
| 6,152,923 A | 11/2000 | Ryan |
| 6,162,220 A | 12/2000 | Nezhat |
| 6,174,309 B1 | 1/2001 | Wrublewski et al. |
| 6,176,857 B1 | 1/2001 | Ashley |
| 6,179,834 B1 | 1/2001 | Buysse et al. |
| 6,179,835 B1 | 1/2001 | Panescu et al. |
| 6,179,837 B1 | 1/2001 | Hooven |
| 6,187,003 B1 | 2/2001 | Buysse et al. |
| 6,190,386 B1 | 2/2001 | Rydell |
| 6,193,709 B1 | 2/2001 | Miyawaki et al. |
| 6,270,497 B1 | 8/2001 | Sekino et al. |
| 6,273,887 B1 | 8/2001 | Yamauchi et al. |
| 6,277,117 B1 | 8/2001 | Tetzlaff et al. |
| 6,296,640 B1 | 10/2001 | Wampler et al. |
| 6,298,550 B1 | 10/2001 | Kirwan, Jr. |
| 6,328,703 B1 | 12/2001 | Murakami |
| 6,334,861 B1 | 1/2002 | Chandler et al. |
| 6,350,264 B1 | 2/2002 | Hooven |
| 6,352,536 B1 | 3/2002 | Buysse et al. |
| 6,398,779 B1 | 6/2002 | Buysse et al. |
| 6,409,725 B1 | 6/2002 | Khandkar et al. |
| 6,451,018 B1 | 9/2002 | Lands et al. |
| 6,458,028 B2 | 10/2002 | Snyder |
| 6,458,130 B1 | 10/2002 | Frazier et al. |
| 6,464,704 B2 | 10/2002 | Schmaltz |
| 6,468,275 B1 | 10/2002 | Wampler et al. |
| 6,500,176 B1 | 12/2002 | Truckai et al. |
| 6,511,480 B1 | 1/2003 | Tetzlaff et al. |
| 6,533,784 B2 | 3/2003 | Truckai et al. |
| 6,554,829 B2 | 4/2003 | Schulze et al. |
| 6,575,968 B1 | 6/2003 | Eggers et al. |
| 6,585,735 B1 | 7/2003 | Lands et al. |
| 6,632,193 B1 | 10/2003 | Davison et al. |
| 6,652,521 B2 | 11/2003 | Schulze |
| 2002/0052599 A1 | 5/2002 | Goble |
| 2002/0115997 A1 | 8/2002 | Truckai et al. |
| 2002/0120266 A1 | 8/2002 | Truckai et al. |
| 2002/0169392 A1 | 11/2002 | Truckai et al. |
| 2002/0177848 A1 | 11/2002 | Truckai et al. |
| 2003/0018327 A1 | 1/2003 | Truckai et al. |
| 2003/0050635 A1 | 3/2003 | Truckai et al. |
| 2003/0055417 A1 | 3/2003 | Truckai et al. |
| 2003/0069579 A1 | 4/2003 | Truckai et al. |
| 2003/0078573 A1 | 4/2003 | Truckai et al. |
| 2003/0078577 A1 | 4/2003 | Truckai et al. |
| 2003/0078578 A1 | 4/2003 | Truckai et al. |
| 2003/0114851 A1 | 6/2003 | Truckai et al. |
| 2003/0125727 A1 | 7/2003 | Truckai et al. |
| 2003/0139741 A1 | 7/2003 | Goble et al. |
| 2003/0144652 A1 | 7/2003 | Baker et al. |

FOREIGN PATENT DOCUMENTS

EP          517 244 B1     3/1996

| | | | |
|---|---|---|---|
| EP | 518 230 B1 | 5/1996 |
| FR | 2536924 A1 | 6/1984 |
| FR | 2647683 A1 | 12/1990 |
| GB | 2037167 A | 7/1980 |
| GB | 2066104 A | 7/1981 |
| GB | 2133290 A | 7/1984 |
| GB | 2161082 A | 1/1986 |
| SU | 342617 | 6/1972 |
| SU | 575103 | 10/1977 |
| WO | WO 93/08754 A1 | 5/1993 |
| WO | WO 94/24949 A1 | 11/1994 |
| WO | WO 94/24951 A1 | 11/1994 |

OTHER PUBLICATIONS

Burton, J.D.K., "New inventions," *The Lancet*, pp. 650-651 (1959).

Nardella, P.C., "Radio Frequency Energy and Impedance Feedback," Proc. SPIE, *Catheter-Based Sensing and Imaging Technology*, 1068:42-48 (1989).

Vallfors et al., "Automatically controlled bipolar electrocoagulation—'COA-COMP'," *Neurosurg. Rev.*, 187-190 (1984).

* cited by examiner

ELECTROSURGICAL JAW STRUCTURE FOR CONTROLLED ENERGY DELIVERY

CROSS-REFERENCES TO RELATED APPLICATIONS

This application is a continuation of U.S. patent application Ser. No. 10/032,867, filed Oct. 22, 2001, and issued as U.S. Pat. No. 6,929,644, titled *Electrosurgical Jaw Structure for Controlled Energy Delivery*, the full disclosure of which is incorporated herein by reference.

BACKGROUND OF THE INVENTION

1. Field of the Invention

This invention relates to electrosurgical jaws and methods for delivering energy to tissue, and more particularly to an instrument working end for grasping tissue that self-modulates energy application to engaged tissues for sealing, welding or coagulating purposes.

2. Description of the Related Art

In various open and laparoscopic surgeries, it is necessary to coagulate, seal or weld tissues. One preferred means of tissue-sealing relies upon the application of electrical energy to captured tissue to cause thermal effects therein for sealing purposes. Various mono-polar and bi-polar radiofrequency (Rf) jaw structures have been developed for such purposes. In a typical bi-polar jaw arrangement, each jaw face comprises an electrode and Rf current flows across the captured tissue between the first and second polarity electrodes in the opposing jaws. While such bi-polar jaws can adequately seal or weld tissue volumes that have a small cross-section, such bi-polar instruments often are ineffective in sealing or welding many types of tissues, such as anatomic structures having walls with irregular or thick fibrous content, bundles of disparate anatomic structures, substantially thick anatomic structures, or tissues with thick fascia layers such as large diameter blood vessels.

Prior art Rf jaws that engage opposing sides of a tissue volume typically cannot cause uniform thermal effects in the tissue, whether the captured tissue is thin or substantially thick. As Rf energy density in tissue increases, the tissue surface becomes desiccated and resistant to additional ohmic heating. Localized tissue desiccation and charring can occur almost instantly as tissue impedance rises, which then can result in a non-uniform seal in the tissue. The typical prior art Rf jaws can cause a further undesirable effects by propagating Rf density laterally from the engaged tissue to cause unwanted collateral thermal damage.

What is needed is an instrument with a jaw structure that can apply Rf energy to tissue in new modalities: (i) to weld or seal tissue volumes that have substantial fascia layers or tissues that are non-uniform in hydration, density and collagenous content; (ii) to weld a targeted tissue region while substantially preventing thermal damage in regions lateral to the targeted tissue; and (iii) to weld a bundle of disparate anatomic structures.

BRIEF SUMMARY OF THE INVENTION

The principal objective of the present invention is to provide an instrument and jaw structure that is capable of controllably applying energy to engaged tissue. As background, the biological mechanisms underlying tissue fusion by means of thermal effects are not fully understood. In general, the application of Rf energy to a captured tissue volume causes ohmic heating (alternatively described as active Rf heating herein) of the tissue to thereby at least partially denature proteins in the tissue. By ohmic heating, it is meant that the active Rf current flow within tissue between electrodes causes frictional or resistive heating of conductive compositions (e.g., water) in the tissue.

One objective of the invention is to denature tissue proteins, including collagen, into a proteinaceous amalgam that intermixes and fuses together as the proteins renature. As the treated region heals over time, the so-called weld is reabsorbed by the body's wound healing process. A more particular objective of the invention is to provide a system that (i) instantly and automatically modulates ohmic heating of tissue to maintain a selected temperature in the tissue, and (ii) to instantly and automatically modulate total energy application between active Rf heating (resulting from tissue's resistance to current flow therethrough) and conductive heating of tissue that results from heat conduction and radiation from resistively heated jaw components.

In general, the various jaw structures corresponding to the present invention all provide an Rf working end that is adapted to instantly and automatically modulate between active Rf heating of tissue and conductive heating of tissue by resistive jaw portions. Thus, the targeted tissue can be maintained at a selected temperature for a selected time interval without reliance of prior art "feedback" monitoring systems that measure impedance, temperature, voltage or a combination thereof.

In an exemplary embodiment, at least one jaw of the instrument defines a tissue-engagement plane that engages the targeted tissue. A cross-section of the jaw inwardly of the engagement plane illustrates that multiple electrically-conductive components comprise the invention for applying energy to tissue. Typically, the engagement plane defines a surface conductive portion (for tissue contact) that overlies a medial portion of a variably resistive material. An exemplary jaw further carries a core conductive material (or electrode) that is coupled to an Rf source and controller. Of particular interest, one embodiment has a variably resistive matrix that comprises a positive temperature coefficient (PTC) material having a resistance (i.e., impedance to electrical conduction therethrough) that changes as it increases in temperature. One type of PTC material is a ceramic that is engineered to exhibit a dramatically increasing resistance above a specific temperature of the material, sometimes referred to as a Curie point or a switching range.

In one embodiment, a jaw of the working end utilizes a medial variably resistive matrix that has a selected switching range, for example a 5°–20° C. range, which approximates a targeted temperature that is suitable for tissue welding. In operation, it can be understood that the engagement plane will apply active Rf energy to (or cause ohmic heating within) the engaged tissue until the point in time that the variably resistive matrix is heated to its selected switching range. When the tissue temperature thus elevates the temperature of the PTC material to the switching range, Rf current flow from the core conductive electrode through to the engagement surface will be terminated due to the temperature increase in tissue and the resistive matrix. This instant and automatic reduction of Rf energy application can be relied on to prevent any substantial dehydration of tissue proximate to the probe's engagement plane. By thus maintaining an optimal level of moisture around the engagement plane, the working end can more effectively apply energy to the tissue—and provide a weld thicker tissues with limited collateral thermal effects.

The working end of the probe corresponding to the invention further provides a suitable cross-section and mass for providing a substantial heat capacity. Thus, when the medial variably resistive matrix is elevated in temperature to its switching range, the matrix can effectively function as a resistive electrode to thereafter passively conduct thermal energy to the engaged tissue volume. Thus, in operation, the working end can automatically modulate the application of energy to tissue between active Rf heating and passive conductive heating of the targeted tissue to maintain the targeted temperature level.

In another preferred embodiment of the invention, the variably resistive matrix can be a silicone-based material that is flexible and compressible. Thus, the engagement surface of one or both jaws can flexibly engage tissue to maintain tissue contact as the tissue shrinks during the welding process. In a related embodiment, the variably resistive matrix can be an open-cell silicone-based material that is coupled to a fluid inflow source for delivering fluid to the engagement plane to facilitate welding of very thin tissue volumes.

The jaws of the invention can operate in mono-polar or bi-polar modalities, with the variably resistive matrix carried in either or both jaws of the working end.

BRIEF DESCRIPTION OF THE DRAWINGS

Other objects and advantages of the present invention will be understood by reference to the following detailed description of the invention when considered in combination with the accompanying Figures, in which like reference numerals are used to identify like elements throughout this disclosure.

DETAILED DESCRIPTION OF THE INVENTION

1. Type "A" Working End for Tissue Sealing

Figure 1:
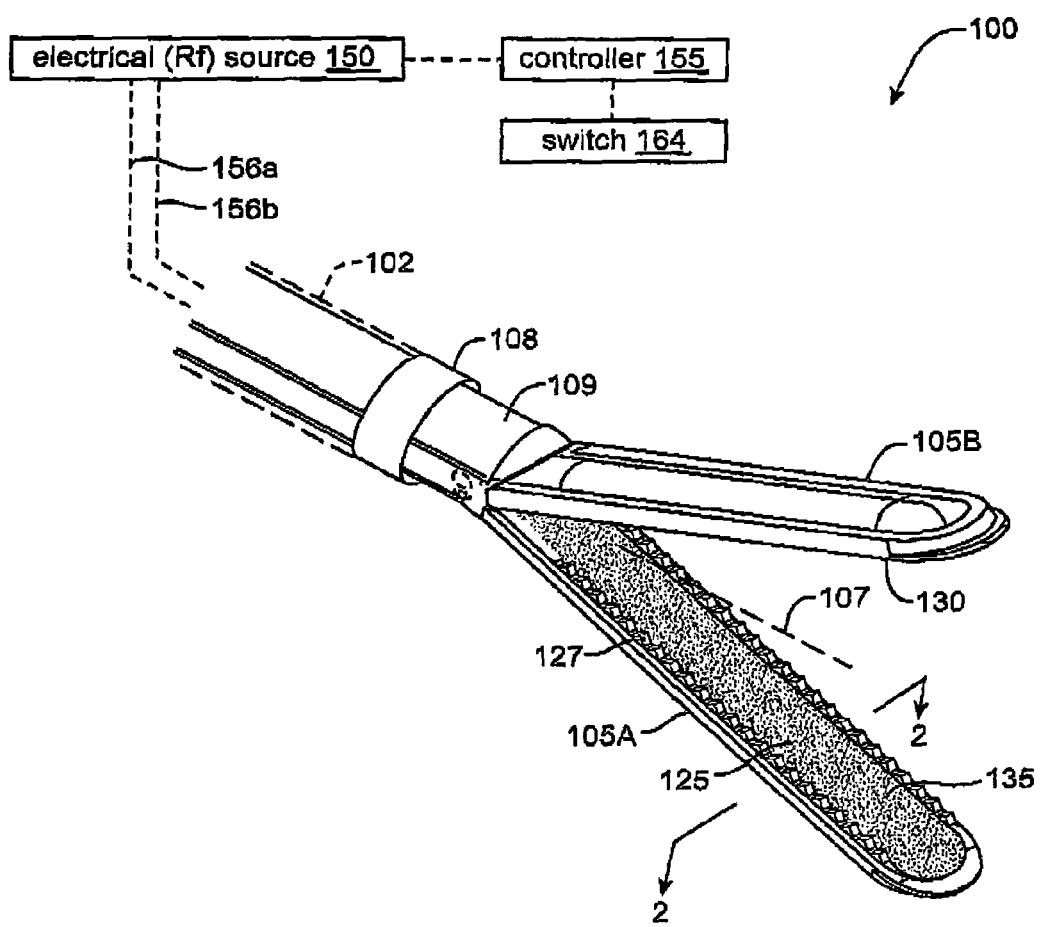
FIG. 1 is perspective view of a Type "A" working end of the invention showing first and second jaws carried at the end of an introducer.
Figure 2:
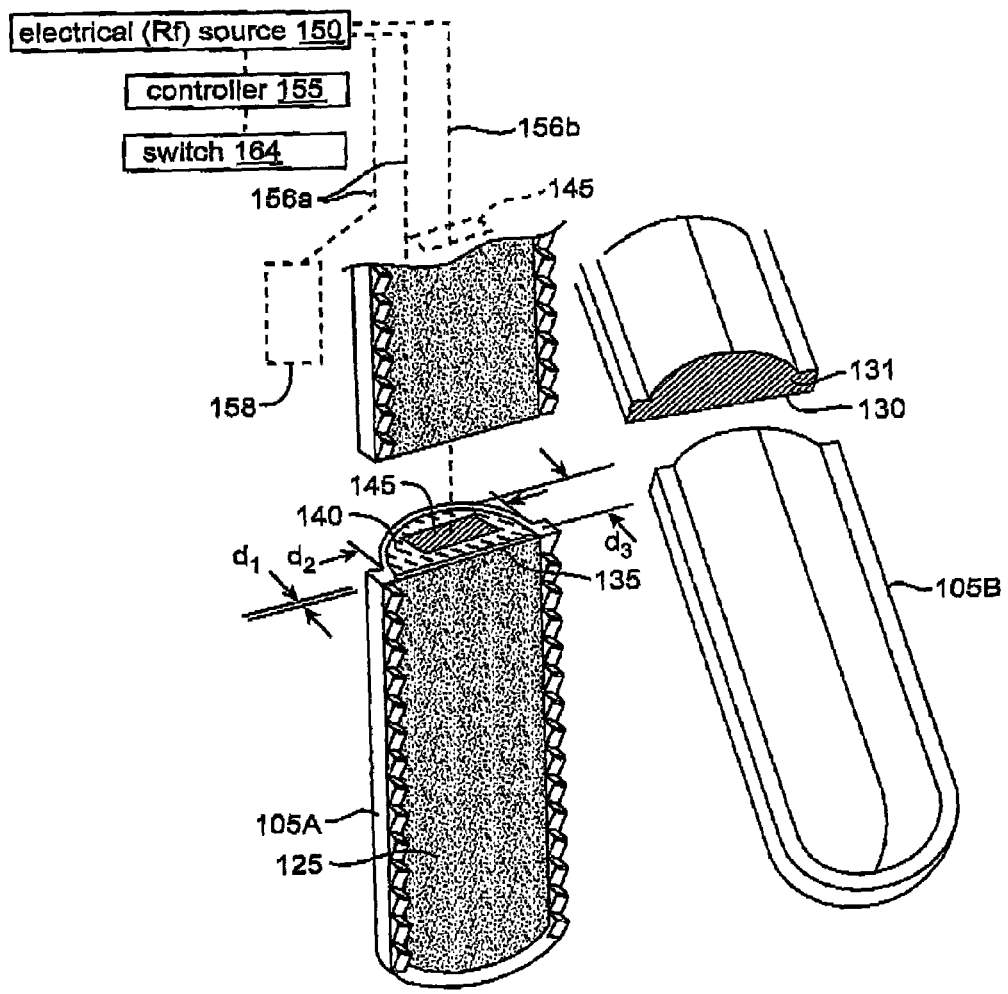
FIG. 2 is a partial sectional view of a portion of the jaws of FIG. 1 taken along line 2—2 of FIG. 1 showing the active electrical energy delivery components corresponding to the invention.

An exemplary Type "A" working end 100 of a surgical grasping instrument is illustrated in FIGS. 1–2 that is adapted for energy delivery for sealing or welding tissue. The working end 100 is carried at the distal end of an introducer portion 102 that can be rigid or flexible in any suitable diameter. For example, the introducer portion 102 can have a diameter ranging from about 3 mm. to 5 mm. (or larger) for use in endoscopic surgical procedures. The introducer portion extends along axis 107 from its proximal end that is connected to a handle (not shown). The working end has first (lower) jaw 105A and second (upper) jaw 105B that are coupled to the distal end 108 of the introducer portion 102. The jaws may both be moveable or a single jaw may move to provide an open position and a closed position wherein the jaws approximate toward axis 107. The opening-closing mechanism can be any type known in the art. For example, a reciprocatable cam-type member 109 can slide over the jaws 105A and 105B to engage the outer surfaces of the jaws, and can be the type of mechanism disclosed in co-pending U.S. patent application Ser. No. 09/792,825 filed Feb. 24, 2001 titled *Electrosurgical Working End for Transecting and Sealing Tissue*, which is incorporated herein by reference.

In the exemplary embodiment of FIG. 2, the first (lower) jaw 105A has a tissue-engaging surface or engagement plane 125 that contacts and delivers energy to a targeted tissue.

The jaws can have any suitable length with teeth or serrations in any location for gripping tissue, and is shown in FIG. 2 with such serrations 127 along the outboard portions of the jaws thus leaving the engagement plane 125 inward of the serrations. In the embodiments described below, the engagement plane 125 generally is shown with a non-serrated surface for clarity of explanation, but the engagement plane 125 itself can be any non-smooth gripping surface.

In the exemplary embodiment of FIG. 2, the engagement surface or plane 125 that delivers energy to tissue extends along an axial length of only the lower jaw 105A, and the tissue-contacting surface 130 of the second jaw 105B is passive and comprises an insulated material 131 or has an insulated surface layer. As will be described below, alternative embodiments corresponding to the invention provide both the first and second jaws with electrically "active" components.

The sectional view of FIG. 2 more particularly illustrates the individual electrically relevant components within the body of the lower jaw for controllably delivering energy to tissue for sealing or welding purposes. The engagement surface 125 of jaw 105A has a conductive surface material indicated at 135 that is both electrically conductive and thermally conductive. For example, the conductive surface layer 135 can be a thin film deposit of any suitable material known in the art (e.g., gold, platinum, palladium, silver, stainless steel, etc.) having any suitable thickness dimension $d_1$, for example, ranging from about of 0.0001" to 0.020". Alternatively, the conductive layer 135 can comprise a machined or cast metal having a more substantial thickness that is conductively bonded to the interior layers described next.

As can be seen in FIG. 2, the jaw 105A has a medial (second) material or matrix 140 that is variably resistive (alternatively called variably conductive herein) and carried inwardly of the surface conductive material 135. Further, the body of jaw 105A carries a (third) interior conductive material or electrode 145 at its core. The medial conductive layer 140 thus is intermediate the engagement plane 125 and the interior conductive material 145. The third conductive material or electrode 145 is coupled by an electrical lead to a remote voltage (Rf) source 150 and optional controller 155. The medial variably resistive matrix 140 can have any suitable cross-sectional dimensions, indicated generally at $d_2$ and $d_3$, and preferably such a cross-section comprises a significant fractional volume of the jaw body to provide a thermal mass for optimizing passive conduction of heat to tissue as will be described below.

It can be easily understood from FIG. 2 that the core conductive material 145 is coupled to, or immediately adjacent to, the medial variably resistive material 140 for conducting electrical energy from the interior conductor to engaged tissue through matrix 140. In FIG. 2, it can be seen that the first, second and third components (indicated at 135, 140, 145) are carried in a structural body component 148 of the jaw 105A that can be any suitable metal with an insulative coating or any other rigid body that can accommodate loads on the jaw as it engages and compresses tissue.

Of particular interest, still referring to FIG. 2, the medial variable conductive matrix 140 comprises a polymeric material having a temperature-dependent resistance. Such materials are typically known in the art as polymer-based temperature coefficient materials, and sometimes specifically described as thermally-sensitive resistors or thermistors that exhibit very large changes in resistance with a small change of body temperature. This change of resistance with a change in temperature can result in a positive coefficient of resistance where the resistance increases with an increase in temperature (PTC or positive temperature coefficient material). The scope of the invention also includes a medial variably conductive matrix 140 of a negative temperature coefficient (NTC) material wherein its resistance decreases with an increase in temperature.

Figure 3:
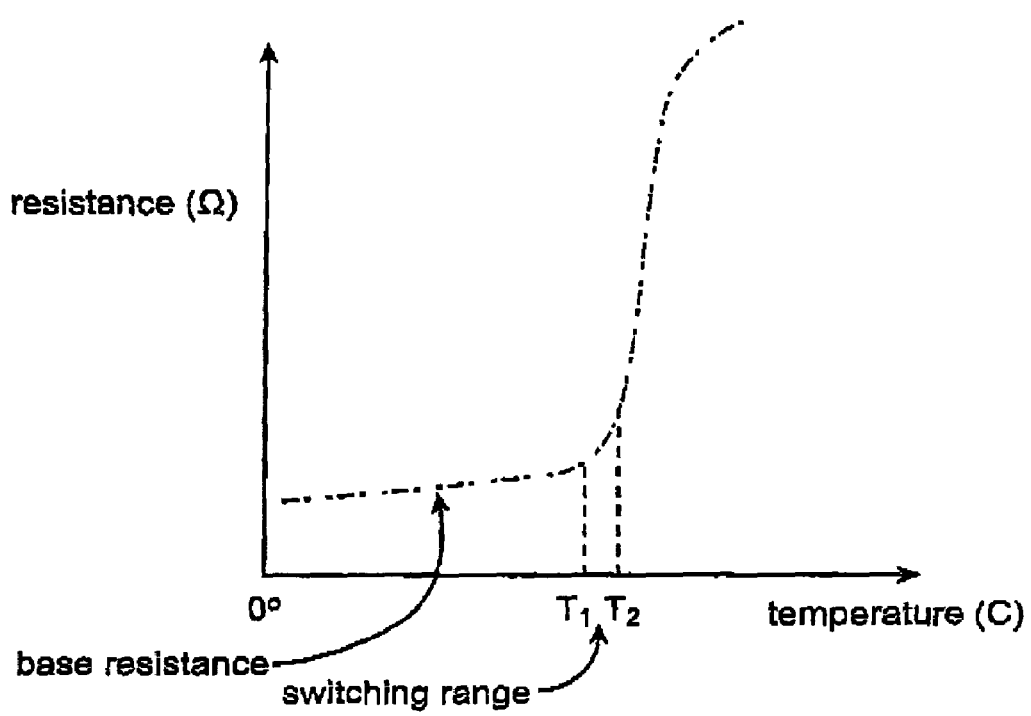
FIG. 3 is a graph of the temperature vs. resistance profile of the positive temperature coefficient (PTC) matrix of the jaws of FIGS. 1–2.
Figure 4:
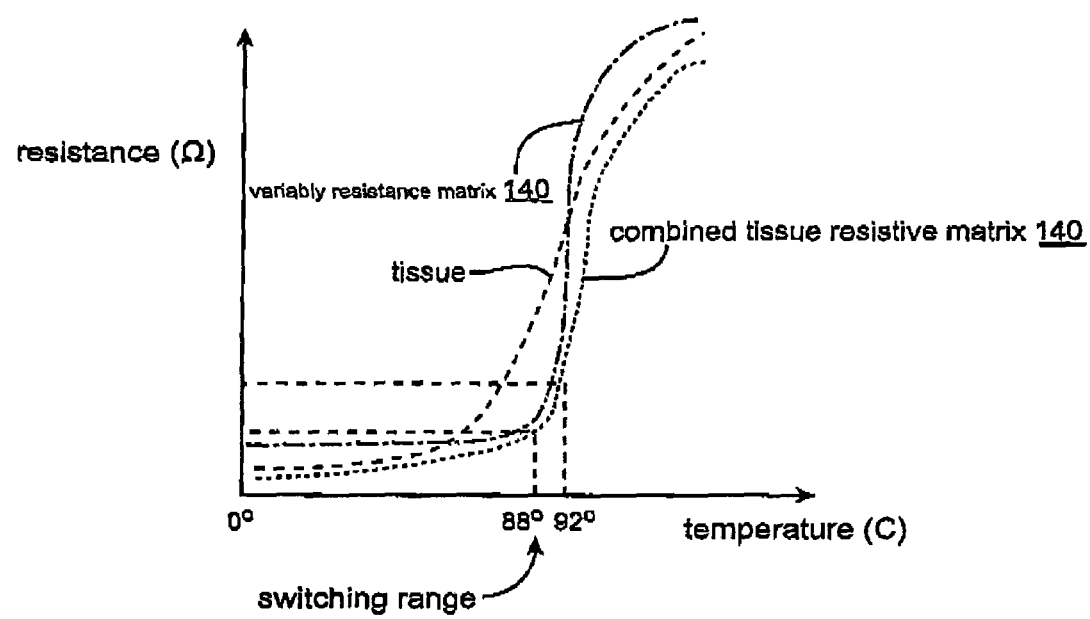
FIG. 4 is a graph showing the temperature-resistance profile of the PTC matrix, the impedance of tissue and the combined resistance of the PTC matrix and tissue that is readable by feedback circuitry.

In one preferred embodiment, the PTC matrix 140 is a ceramic layer that can be engineered to exhibit unique resistance vs. temperature characteristics and can maintain a very low base resistance over a wide temperature range, with a dramatically increasing resistance above a specific temperature of the material (sometimes referred to as a Curie point or switching range; see FIG. 3). One aspect of the invention relates to fabrication of the medial PTC matrix 140 to have a selected switching range between a first temperature ($T_1$) and a second temperature ($T_2$) that approximates the targeted tissue temperature in the contemplated tissue sealing or welding objective. The selected switching range, for example, can be any substantially narrow 1°–10° C. range that is determined to be optimal for tissue sealing or welding (e.g., any 5° C. range between about 65°–200° C.). A more preferred switching range can fall within the larger range of about 80°–100° C.

In operation, it can be understood that the delivery of Rf energy to the interior conductor 145 will be conducted through the variably conductive matrix 140 and the engagement plane 125 to thereby apply Rf energy (or active ohmic heating) to tissue engaged between the jaws 105A and 105B (see FIG. 2). After the engaged tissue is elevated in temperature by such active Rf heating, the lower jaw's conductive surface layer 135 and the medial conductive layer 140 will be elevated to the selected switching range. Thereafter, the mass of the body will be modulated in temperature, similar to the engaged tissue, at or about the selected switching range. Thereafter, the jaws body will conduct or radiate thermal effects to the engaged tissue.

In other words, the critical increase in temperature of the variably resistive matrix 140 is typically caused by the transient high temperature of tissue that is caused by active Rf heating of the tissue. In turn, heat is conducted back through the layer of the first conductive material 135 to medial matrix 140. A suitable variably resistive PTC material can be fabricated from high purity semi-conducting ceramics, for example, based on complex titanate chemical compositions (e.g., $BaTiO_3$, $SrTiO_3$, etc.). The specific resistance-temperature characteristics of the material can be designed by the addition of dopants and/or unique materials processing, such as high pressure forming techniques and precision sintering. Suitable variably resistive or PTC materials are manufactured by a number of sources, and can be obtained, for example from Western Electronic Components Corp., 1250-A Avenida Acaso, Camarillo, Calif. 93012. Another manner of fabricating the medial conductive material 140 is to use a commercially available epoxy that is doped with a type of carbon. In fabricating a substantially thin medial conductive layer 140 in this manner, it is preferable to use a carbon type that has single molecular bonds. It is less preferable to use a carbon type with double bonds which has the potential of breaking down when used in thin layers, thus creating the potential of an electrical short circuit between conductive portions 145 and 135.

As can be seen in FIG. 2, the core conductive material or electrode 145 is operatively connected to the voltage (Rf) source 150 by a first electrical lead 156a that defines a first polarity of the Rf source. In this preferred embodiment, the conductive engagement surface 135 is coupled to a second electrical lead 156b that defines a second or opposing polarity of the Rf source 150. A ground pad indicated at 158 in FIG. 2 first lead 156a to accomplish a preferred method of the invention, as will be described below.

The manner of utilizing the working end 100 of FIG. 2 to perform a method of the invention can be understood as engaging and compressing tissue between the first and second jaws 105A and 105B and thereafter applying active Rf energy to the tissue to maintain a selected temperature for a selected time interval. For example, the instrument is provided with a working end that carries a medial variably conductor matrix 140 (see FIG. 2) that has a switching range at or about 90° C. at which its resistance increases greater than about 5% (and can be as much as 1,000,000% or more) above its low base resistively with a change in temperature of about 5° C. or less (see FIG. 3).

With the jaws in the closed position and the engagement plane 125 engaging tissue, the operator actuates a switch 164 that delivers Rf energy from the voltage (Rf) source 150 to the interior conductor 145. At ambient tissue temperature, the low base resistance of the medial conductive matrix 140 allows unimpeded Rf current flow from the voltage source 150 through the engagement surface 125 (and conductor layer 135) and tissue to return electrical lead 156a that is coupled to ground pad 158. It can be understood that the engaged tissue initially will have a substantially uniform impedance to electrical current flow, which will increase substantially in proximity to engagement surface 125 as the engaged tissue loses moisture due to the active Rf delivery.

Following an arbitrary time interval, the impedance of tissue proximate to engagement surface 125 typically will be elevated, and the higher tissue temperature will instantly conduct heat to the medial PTC matrix 140. In turn, the medial PTC layer 140 will reach its switching range and terminate Rf current flow from the core conductor 145 to the engagement surface 125. Such automatic reduction of active Rf energy application will prevent any substantial dehydration of tissue proximate to the engagement plane 125. By thus maintaining the desired level of moisture in tissue proximate to the engagement plane 125, the working end can more effectively apply energy to the tissue. Such energy application can extend through thick engaged tissue volumes while causing very limited collateral thermal effects. Thereafter, as the temperature of tissue proximate to engagement surface 125 falls by thermal relaxation and the lack of an Rf energy density, the temperature of the medial conductive matrix 140 will thus fall below the threshold of the selected switching range. This effect, in turn, will cause Rf current to again flow through the assembly of conductive layers 145, 140 and 135 to the engaged tissue to again increase the tissue temperature by active Rf heating. By the above-described mechanisms of causing the medial variably resistive matrix 140 to hover about its selected switching range, the actual Rf energy applied to the engaged tissue can be precisely modulated to maintain the desired temperature in the tissue.

Of particular interest, in one embodiment, the polymer matrix that comprises the medial conductor portion 140B is doped with materials to resistively heat the matrix as Rf energy flow therethrough is reduced. Thus, the thermal mass of the jaws which are elevated in temperature can deliver energy to the engaged tissue by means of greater passive conductive heating—at the same time Rf energy delivery causes lesser active tissue heating. This balance of active Rf heating and passive conductive (or radiative) heating can maintain the targeted temperature for any selected time interval.

In summary, one method of the invention comprises the delivery of Rf energy from a voltage source 150 to a conductive jaw surface 135 through a thermally-sensitive resistor material 140 wherein the resistor material has a selected switching range that approximates a targeted temperature for tissue sealing or welding. In operation, the working end automatically modulates active Rf energy density in the tissue as the temperature of the engaged tissue conducts heat back to the thermally-sensitive resistor material 140 to cause its temperature to reach the selected switching range. In this range, the Rf current flow will be reduced, with the result being that the tissue temperature can be maintained in the selected range without the need for thermocouples or any other form of feedback circuitry mechanisms to modulate Rf power from the source. Most important, it is believed that this method of the invention will allow for immediate modulation of actual Rf energy application along the entire length of the jaws, which is to be contrasted with prior art instruments that utilize a temperature sensor and feedback circuitry. Such sensors or thermocouples measure temperature only at a single location in the jaws, which typically will not be optimal for energy delivery over the length of the jaws. Such temperature sensors also suffer from a time lag. Further, such temperature sensors provide only an indirect reading of actual tissue temperature—since a typical sensor can only measure the temperature of the electrode.

Another method of the invention comprises providing the working end with a suitable cross-section of variably resistive matrix 140 so that when it is elevated in temperature to a selected level, the conductive matrix 140 effectively functions as a resistive electrode to passively conduct thermal energy to engaged tissue. Thus, in operation, the jaws can automatically modulate the application of energy to tissue between active Rf heating and passive conductive heating of the targeted tissue at a targeted temperature level.

FIG. 3 illustrates another aspect of the method of the invention that relates to the Rf source 150 and controller 155. A typical commercially available radiofrequency generator has feedback circuitry mechanisms that control power levels depending on the feedback of impedance levels of the engaged tissue. FIG. 3 is a graph relating to the probe of present invention that shows: (i) the temperature-resistance profile of the targeted tissue, (ii) the temperature-resistance profile of the PTC conductive matrix 140 of the probe, and (iii) the combined temperature-resistance profile of engaged tissue and the PTC conductive matrix. In operation, the Rf source 150 and controller 155 can read the combined impedance of the engaged tissue and the PTC conductive layer which will thus allow the use of the instrument with any typical Rf source without interference with feedback circuitry components.

2. Type "B" Jaw Structures

A series of exemplary Type "B" jaw structures 200a–200i corresponding to the invention are illustrated in FIGS. 5–12. Each set of paired first and second jaws, 205A and 205B, are shown in sectional view to illustrate more specifically how a thermally-dependent variably resistive layer (indicated at 240 in FIGS. 5–12) can be configured to cooperate with at least one electrode to (i) apply active Rf energy to tissue engaged between the jaws while the temperature of the variably resistive matrix is below its switching range, and (ii) to cause modulation of both active and passive heating when the variably resistive matrix hovers about its switching range.

Figure 5:
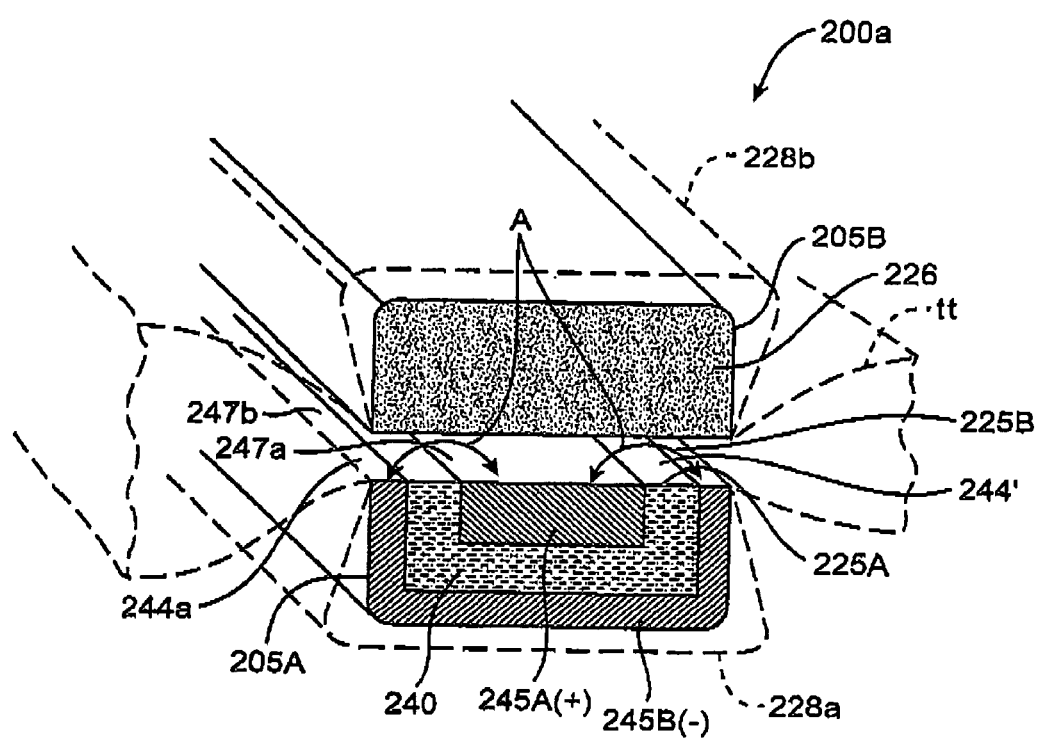
FIG. 5 is a sectional view of a Type "B" jaw structure that carries exposed first and second polarity electrodes and a variably resistive or PTC matrix in an engagement surface of a first jaw with an insulated second jaw, the first and second polarity electrodes adapted, in part, for bi-polar Rf energy application to engaged tissue.

FIG. 5 illustrates working end 200a wherein lower (first) jaw 205A defines an engagement plane 225A that contacts tissue. In this embodiment, the upper (second) jaw 205B defines a tissue-contacting plane 225B that is a surface of an insulator material 226. The structural components of the jaws indicated at 228a and 228b, if required for strength, are of an insulated material or separated from the electrical body components by an insulative layer. Now turning to the active components of the working end 200a, the thermally-dependent resistive layer 240 is exposed to the engagement plane 225A at regions 244a and 244a'. In this embodiment of FIG. 5, the thermally-dependent resistive layer 240 is intermediate to the opposing polarity electrodes 245A and 245B as defined by the circuitry coupled to voltage source 150 (see FIG. 1). For convenience, the electrodes are indicated throughout this disclosure as positive (+) and (−) polarities at a particular point in time. The electrodes 245A and 245B have surface portions 247a and 247b exposed in the engagement plane of the lower jaw. It should be appreciated that the size and shape of structural body components 228a–228b can be varied, and may not be required at all. For example, a jaw as depicted in FIG. 5 can use a substantially strong metal for electrode 245A which can comprise the structural body component of the jaw, with or without a thin insulative coating outside the engagement plane 225A. For clarity of explanation, the gripping elements that are typically used in the jaw surface are not shown.

It can be understood from FIG. 5 that active heating of the targeted tissue tt (phantom view) will occur generally from current flow between first polarity electrode 245A and second polarity electrode 245B (see arrows A). Such current flow also can cooperate with a separate but optional "ground-pad" used as a return electrode (cf. FIG. 2). It can be further understood that the elevation of the tissue temperature of the medial PTC matrix 240 will then modulate energy application between (i) active Rf heating, and (ii) passive or conductive heating. For this reason, in this embodiment as the others described next, the medial PTC matrix 240 preferably comprises a substantial portion of the jaw body for retaining heat for such conductive heating.

Figure 6:
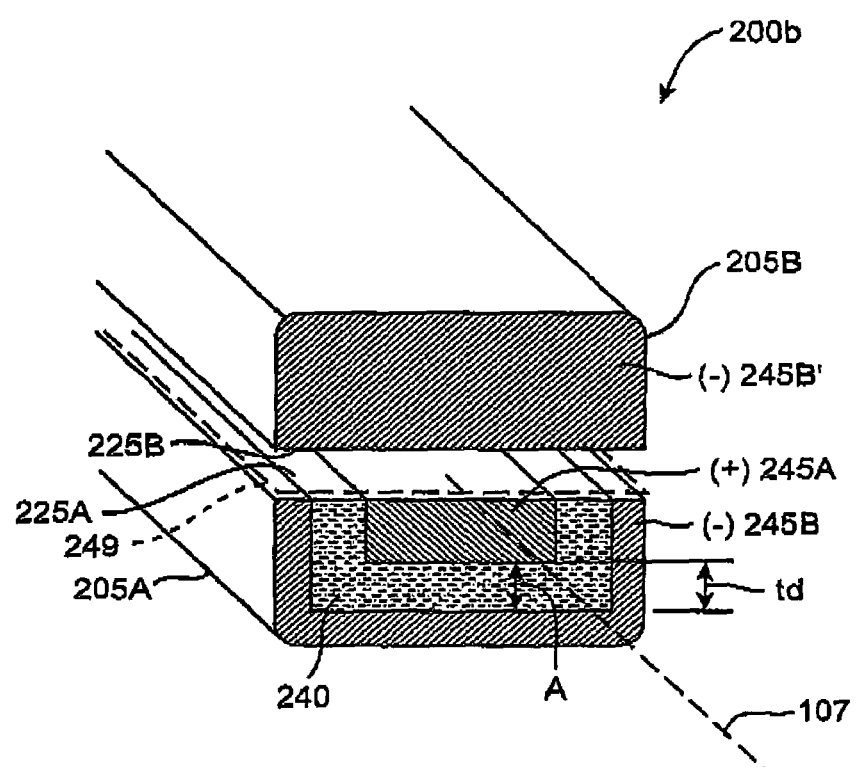
FIG. 6 is a sectional view of an alternative Type "B" jaw structure similar to FIG. 5 that carries cooperating first and second polarity electrodes in both jaws, and a variably resistive matrix in a single jaw.

FIG. 6 illustrates working end 200b with the lower (first) jaw 205A defining 20 engagement plane 225A and the upper (second) jaw 205B defining engagement plane 225B. This embodiment is very similar to the embodiment of FIG. 5, except that the upper engagement plane 225B comprises a surface of an active conductive body indicated at 245B' that is coupled to a voltage source. The electrode 245B' has a polarity common with electrode 245B, or alternatively can have a polarity common with electrode 245A (not shown). It can be understood from FIG. 6 that active heating of tissue engaged between the jaws will occur as current flows between second polarity electrodes 245B–245B' and the first polarity electrode 245A. The working can also cooperate with a separate "ground-pad" that functions as a return electrode (not shown). As described previously, the elevation of the temperature of medial PTC matrix 240 again will modulate energy application between (i) active Rf heating, and (ii) passive or conductive heating about its selected switching range. It should be appreciated that jaws 205A and 205B as depicted FIG. 6 with opposing polarity electrodes in direct opposition to one another can be provided with further means for preventing the electrodes from contacting each other as the jaws are pressed together. The perimeter of the jaws or the jaw's engagement planes can carry surface elements indicated at 249 (phantom view) that prevent contact of the opposing polarity electrodes. For example, the active electrode surfaces can be slightly recessed relative to such elements 249.

Figure 7A:
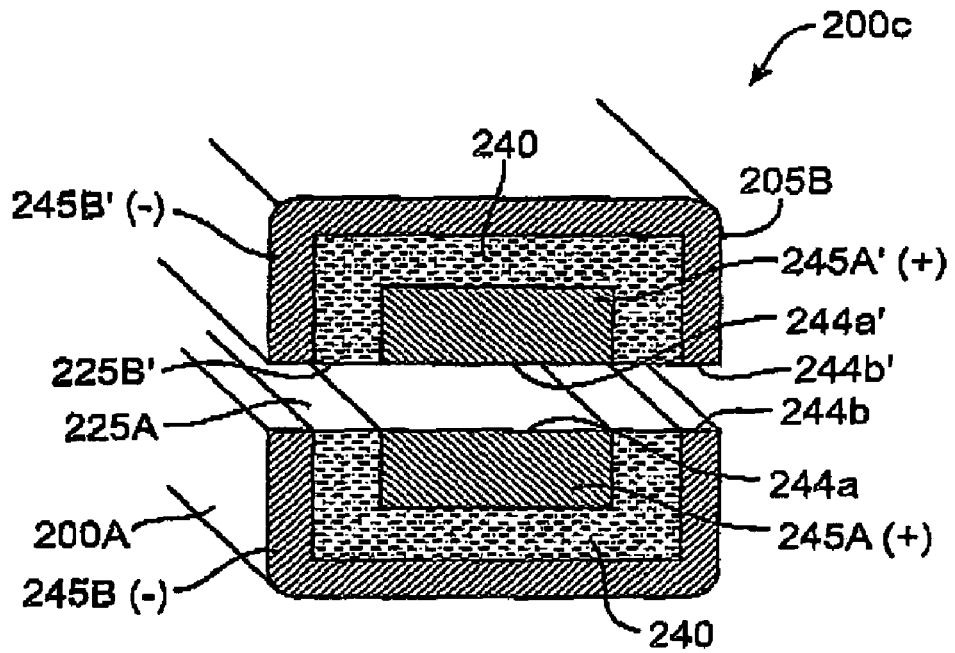
FIGS. 7A–7B are sectional views of another alternative Type "B" jaw structure similar to FIG. 6 that carry cooperating first and second polarity electrodes in both jaws, together with a variably resistive matrix in both jaws.
Figure 7B:
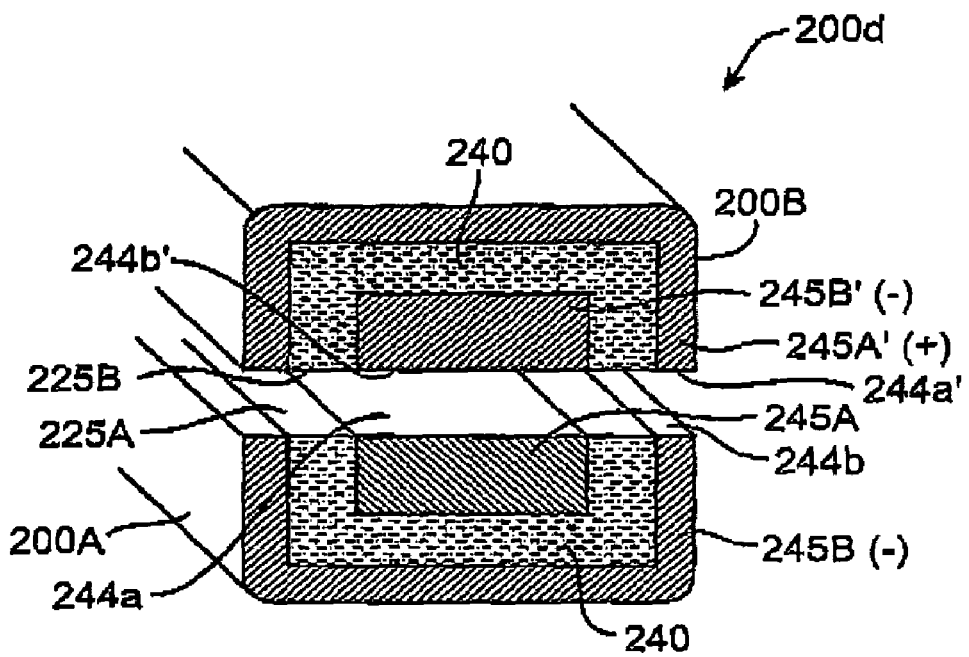

FIGS. 7A–7B illustrate working ends 200c and 200d that are similar and show optional configurations of jaws 205A and 205B that define engagement planes 225A and 225B, respectively. Each jaw in the embodiments of FIGS. 7A–7B carry opposing polarity electrodes with an intermediate layer of a thermally-dependent resistive matrix 240. In FIG. 7A, electrodes 245A and 245B have exposed surfaces 244a and 244b in the lower jaw's engagement plane 225A. Similarly, electrodes 245A' and 245B' have exposed surfaces 244a' and 244b' in engagement plane 225B of the upper jaw. The electrode arrangement of FIG. 7B differs only in the spatial location of the opposing polarity electrode surfaces. In use, it can be understood how Rf active heating of engaged tissue will occur as current flows between first polarity electrodes in each jaw—and between the jaws. Again, the elevation of the temperature of medial PTC matrix 240 will modulate energy application between active Rf heating and passive heating at the selected switching range.

In another similar electrode arrangement (not shown), a plurality of common polarity electrodes can be exposed in an engagement surface with a phase shift in the voltage delivered to such electrodes as provided by the voltage source or sources. Such phase shift electrodes can cooperate with a return electrode in either jaw's engagement surface and/or a ground pad. The paired jaw's engagement surfaces also can be configured with mirror image electrodes, which can be phase shift electrodes which can reduce capacitive coupling among such electrode arrangements. In general, such phase shift features can be combined with any of the working ends of FIGS. 6–12.

Figure 8:
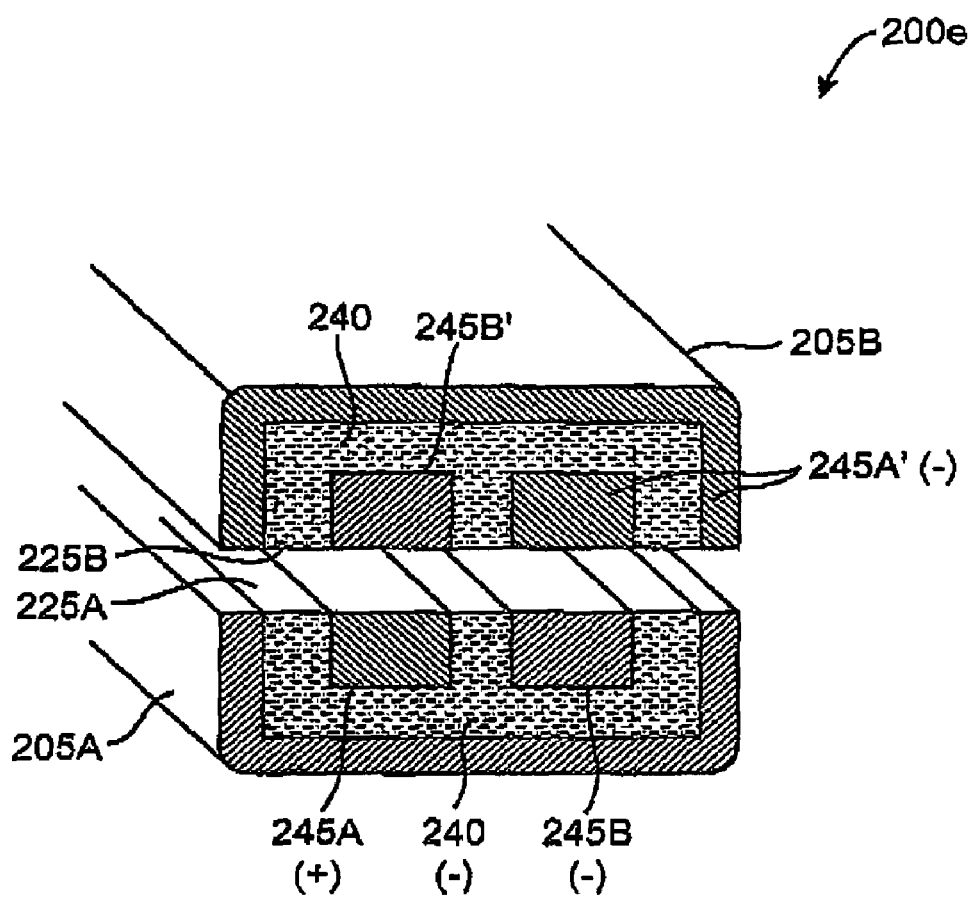
FIG. 8 is a sectional view of another Type "B" jaw structure similar to FIG. 6 that carry cooperating first and second polarity electrodes in both jaws, together with a variably resistive matrix in both jaws.
Figure 9:
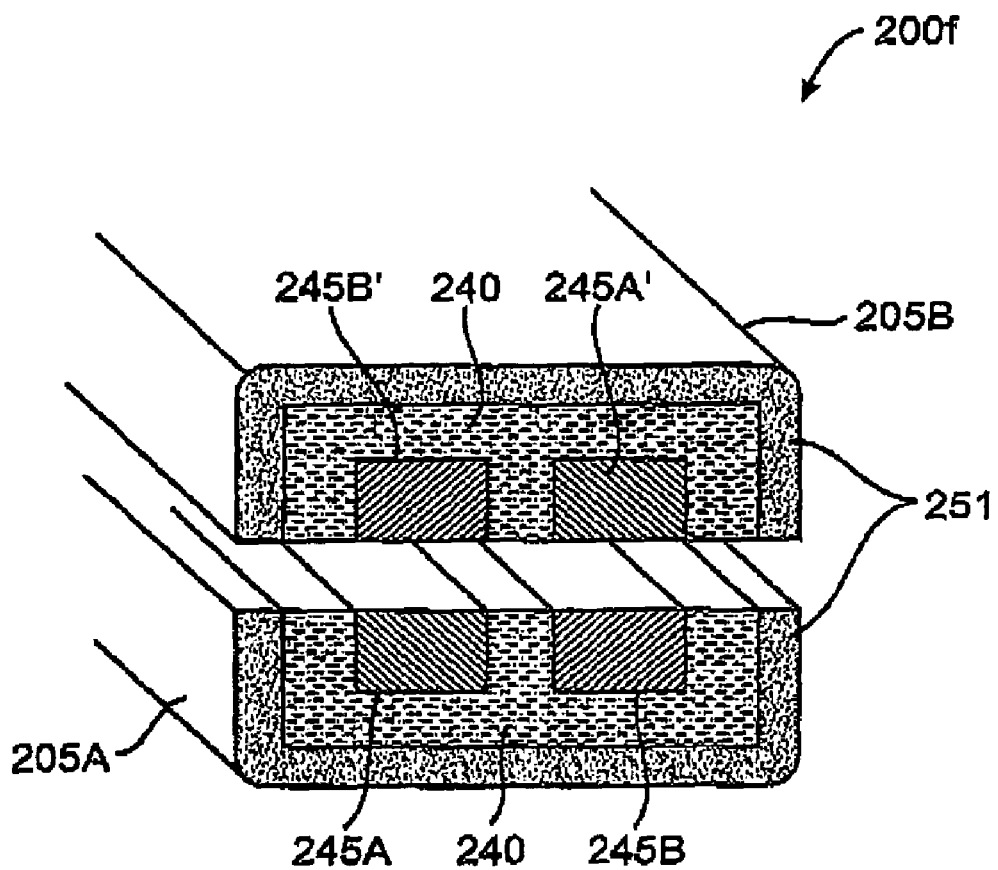
FIG. 9 is a sectional view of another Type "B" jaw structure similar to FIG. 8 that carries cooperating first and second polarity electrodes in each jaws, together with a variably resistive matrix in each jaw and an insulative outer layer.

FIG. 8 illustrates a sectional view of another embodiment of working end 200e with jaws 205A and 205B that define engagement planes 225A and 225B, respectively. In this embodiment, each jaw's engagement plane carries at least two spaced apart electrode surfaces with opposing polarities. For example, lower jaw 205A carries first polarity electrodes 245A and second polarity electrode 245B (collectively). Between the electrodes 245A and 245B is an intermediate thermally-dependent resistive matrix 240. The upper jaw 205B carries first polarity electrodes 245A' (collectively) and second polarity electrode 245B' with thermally-dependent resistive matrix 240 therebetween. Such a jaw configuration will modulate the application of energy to tissue as described previously. FIG. 9 illustrates a sectional view of the jaws of working end 200f which is similar to FIG. 8 except that the jaws have an outer perimeter of a insulator material indicated at 251.

Figure 10:
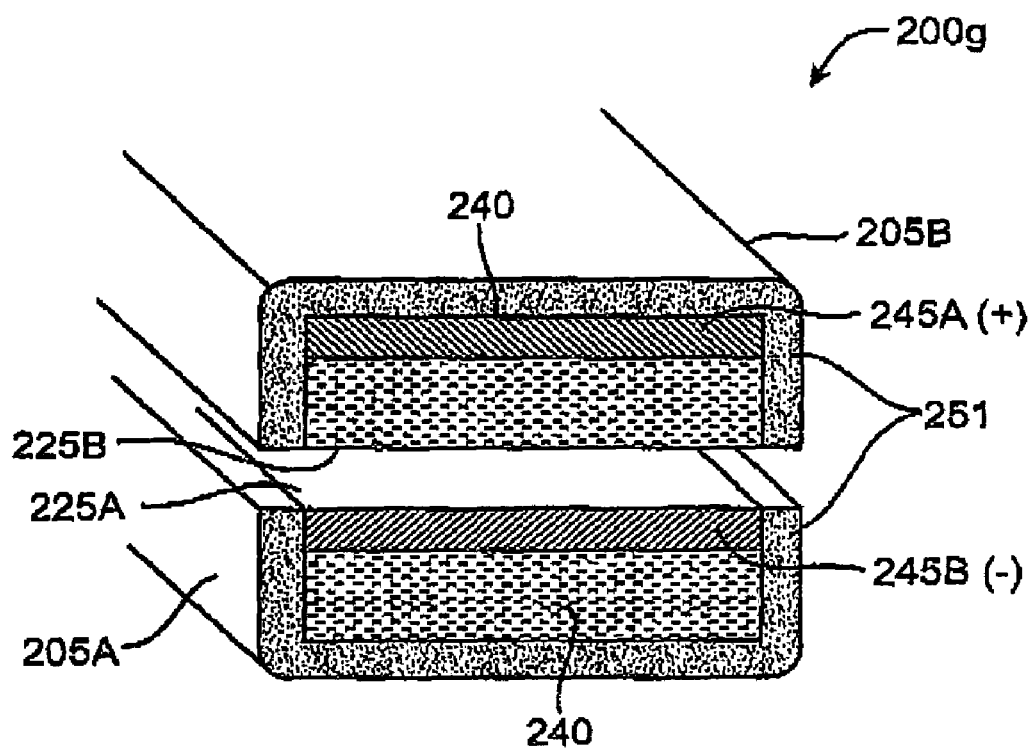
FIG. 10 is a sectional view of another Type "B" jaw structure similar to FIG. 8 that has a first engagement plane with an exposed first polarity electrode and an interior variably resistive matrix and a second engagement plane with an exposed variably resistive matrix and an interior second polarity electrode, each jaw having an insulative outer layer.
Figure 11:
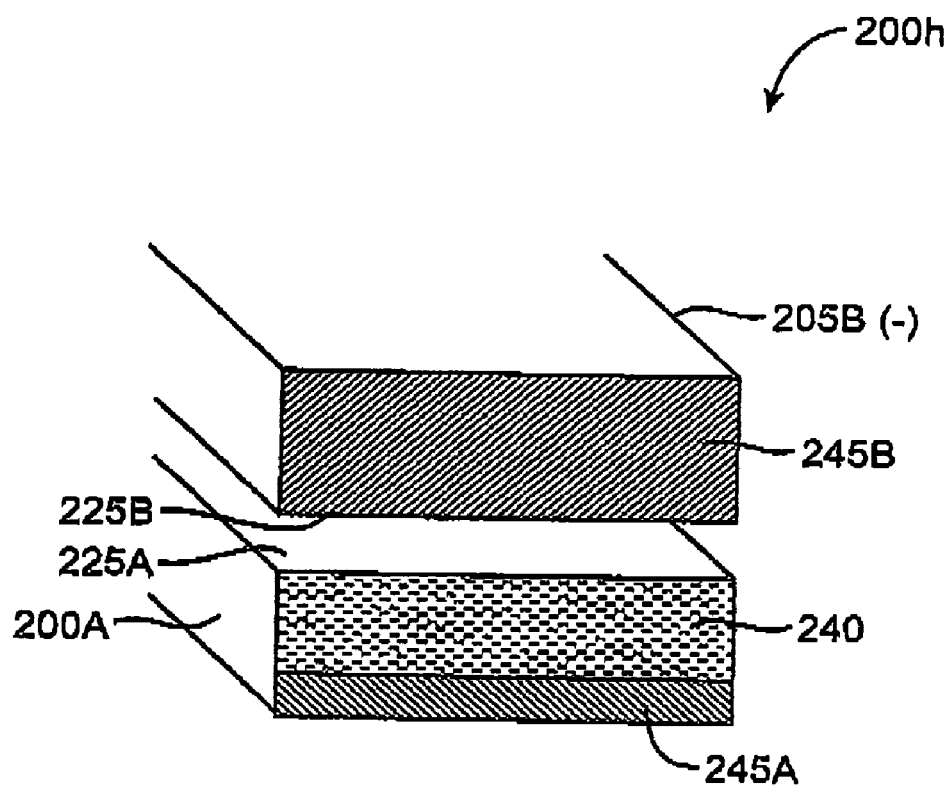
FIG. 11 is a sectional view of yet another Type "B" jaw structure that has a first engagement plane with an exposed variably resistive matrix and an interior first polarity electrode, a second engagement plane with an exposed second polarity electrode.

FIGS. 10 and 11 illustrate sectional views of other embodiments of working end 200g and 200h with jaws 205A and 205B that define engagement planes 225A and 225B, respectively. In these embodiments, one jaw's engagement plane has an active exposed electrode surface indicated at 245B, while the opposing jaw carries an opposing polarity electrode 245A at its interior with a thermally-dependent resistive matrix 240 at that jaw's engagement surface. The jaw assembly of FIG. 10 further shows an optional insulative layer 251 about the exterior of the jaws. The resistive matrix comprises a substantial portion of the jaw's mass, and thus is adapted to modulate the application of energy to tissue as described previously.

Figure 12:
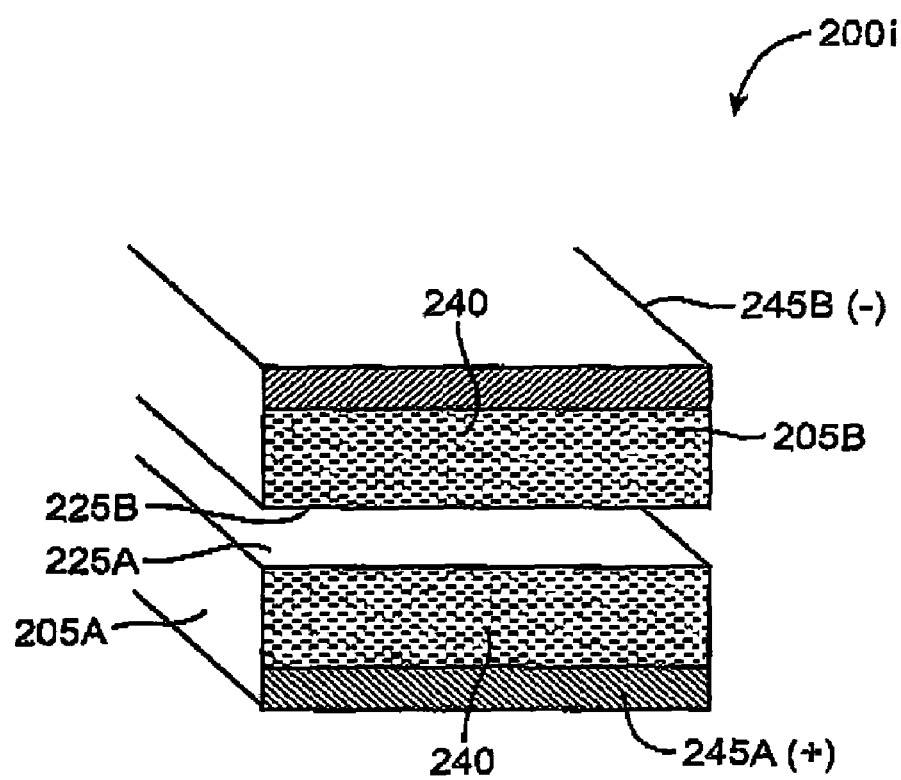
FIG. 12 is a sectional view of another Type "B" jaw structure that has a first and second engagement planes with an exposed variably resistive matrix and interior first and second polarity electrode, respectively.

FIG. 12 illustrates another sectional view of a jaw assembly 200I corresponding to the invention with jaws 205A and 205B that define engagement planes 225A and 225B, respectively. In this embodiment, each jaw's engagement plane 225A and 225B comprises a surface of a thermally-dependent resistive matrix 240 with neither of the opposing polarity electrodes 245A and 245B being exposed for tissue contact.

3. Type "C" Jaw Structure for Sealing Tissue

Figure 13:
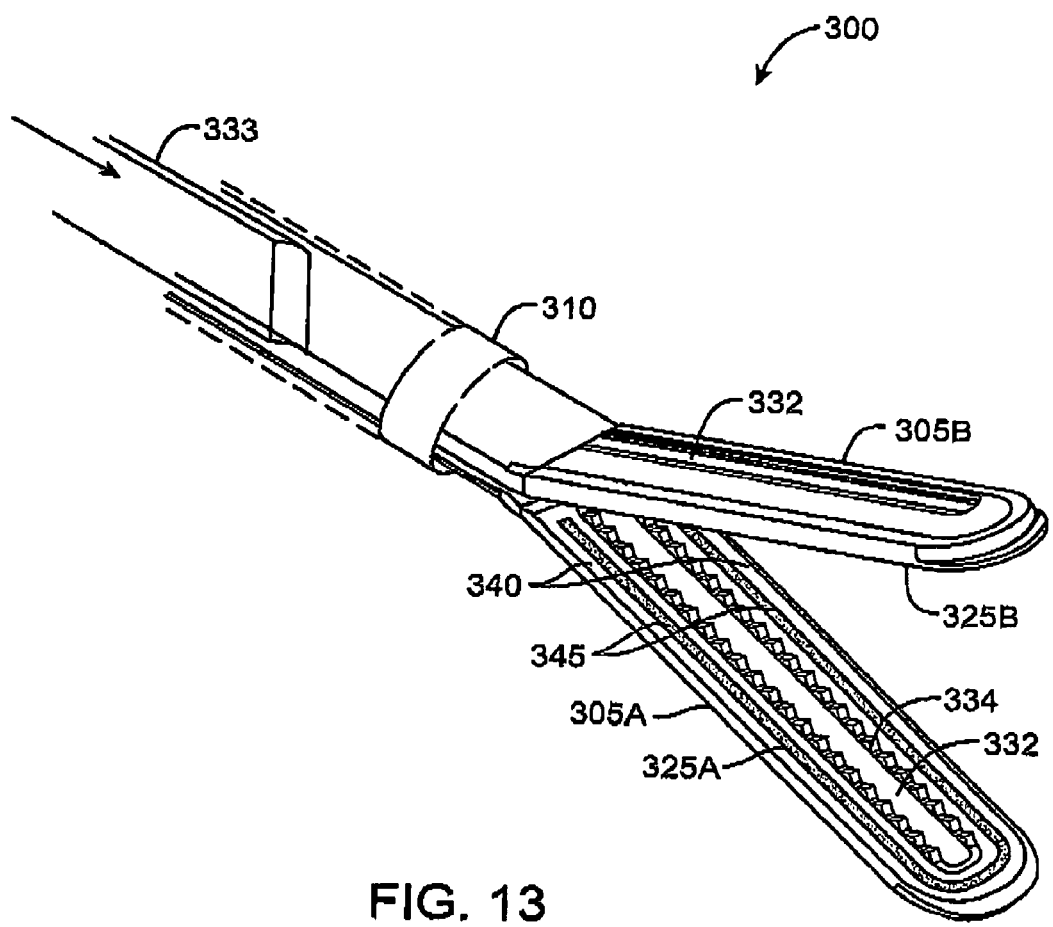
FIG. 13 is a perspective view of a Type "C" working end in accordance with the invention that has a jaw engagement plane with a variably resistive (PTC) material that is flexible or compressible.
Figure 14:
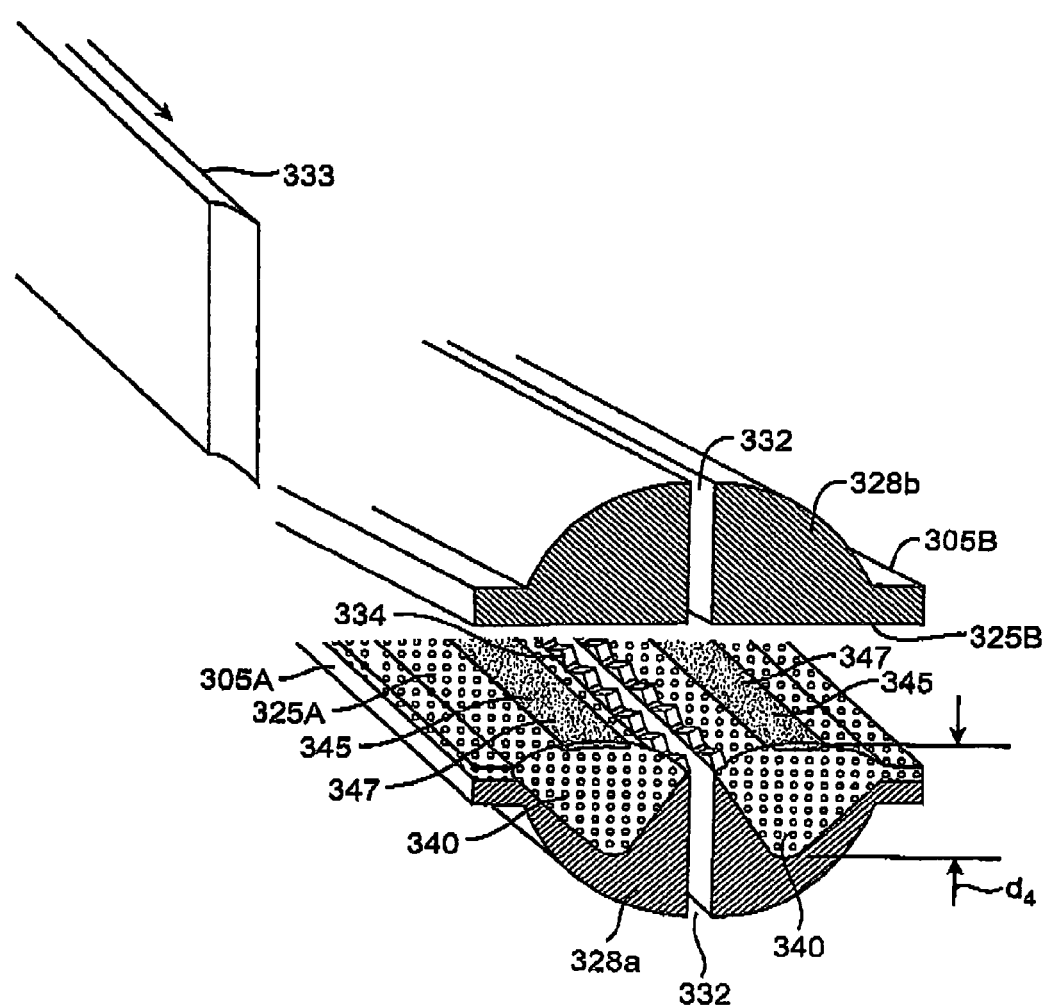
FIG. 14 is a sectional view of the jaws of FIG. 13 showing the variably resistive (PTC) material and exposed electrode surfaces.

An exemplary Type "C" jaw structure 300 carried by introducer 310 corresponding to the invention is illustrated in FIGS. 13–14. The Type "C" system differs in that it utilizes a different form of thermally-dependent resistive layer (indicated at 340 in FIGS. 13–14) that is an elastomer, for example a silicon-based sponge-type material that can be resilient or compressible. More in particular, FIG. 13 illustrates working end 300 with lower (first) jaw 305A defining engagement plane 325A that contacts tissue. The upper (second) jaw 305B defines a tissue-contacting plane 325B that is a surface of an insulator material 326, but it can also carry electrically conductive components as generally depicted in FIGS. 6–12. The jaw structure of FIG. 13 further shows that it is configured with a central channel or slot 332 that is adapted to accommodate a reciprocatable tissue-cutting member 333 for transecting sealed tissue. Such a moveable cutting member 333 is actuated from the instrument handle (not shown) as is known in the art. The cutting member 333 can be a sharp blade or an Rf cutting electrode that is independently coupled to a high voltage Rf source. This embodiment shows tissue-gripping serrations 334 along an inner portion of the jaws, but any location is possible. It should be appreciated that electrode components and thermally-dependent resistive components of the invention can be adapted for any jaws, or left-side and right-side jaw portions, in (i) conventional jaws for tissue sealing or (ii) combination jaws for sealing-transecting instruments. In the embodiment depicted in FIGS. 13–14, the structural body of the jaws 328a and 328b again are preferably of an insulated material or separated from the electrically-connected materials by an insulative layer.

A principal purpose for providing a flexible variably conductive matrix 340 is to dynamically adjust the pressure of the engagement plane 325A against the tissue volume that is compressed between the jaws. It is believed useful to provide a dynamic engagement plane since tissue may shrink during a sealing procedure. The repose or untensioned shape of the variably conductive matrix 340 is shown as being convex, but also can be flat in cross-section or it can have a variety of different geometries or radii of curvature.

Of particular interest, the objective of a resilient jaw surface has resulted in the development of an assembly of materials that can provide a flexible and resilient engagement plane 325A at the surface of a resilient variably resistive material 340. In the embodiment of FIGS. 13–14, it can be seen that the conductive portion or electrode 345 is a thin metallic layer or member bonded to the variably resistive matrix 340, which defines exposed surfaces 347 in the engagement plane 325A. The conductive electrode 325 again coupled to electrical source 150 and controller 155, as described previously.

Of particular interest, the variably resistive matrix 340 comprises a silicone material that can function as a PTC-type resistive matrix in the same manner as the above-described ceramic materials. More in particular, one embodiment of the variably resistive matrix 340 can be fabricated from a medical grade silicone that is doped with a selected volume of conductive particles, e.g., carbon or graphite particles. By weight, the ratio of carbon to silicone can range from about 90/10 to about 30/70 to provide various selected switching ranges wherein the inventive composition then functions as a positive temperature coefficient (PTC) material. More preferably, the matrix is form about 40% to 80% carbon with the balance being silicone. As described previously, carbon types having single molecular bond are preferred. One preferred composition has been developed to provide a switching range of about 75° C. to 90° C. has about 50%–60% carbon with the balance being silicone. The variably resistive matrix 340 can have any suitable thickness dimension indicated at $d_4$, ranging from about 0.01" to 0.25" depending on the cross-section of the jaws.

The electrode 345 that is exposed in engagement plane 325A can be a substantially thin rigid metal, flexible foil, or a substantially flexible thin metallic coating. Such a thin flexible coating can comprise any suitable thin-film deposition, such as gold, platinum, silver, palladium, tin, titanium, tantalum, copper or combinations or alloys of such metals, or varied layers of such materials. A preferred manner of depositing a metallic coating on the polymer element comprises an electrolysis plating process known in the art, such as provided by Micro Plating, Inc., 8110 Hawthorne Dr., Erie, Pa. 16509-4654. The thickness of the metallic coating can range between about 0.0001" to 0.005". Other similar electroplating or sputtering processes known in the art can be used to create a thin film coating.

In operation, the working end of will function as described in the Types "A" and "B" embodiments. The elevation of the tissue temperature will conduct heat directly to the PTC matrix 340 and then will modulate energy application between (i) active Rf heating, and (ii) passive or conductive heating. In addition, the resiliency of the PTC matrix 340 will maintain substantially uniform pressure against the tissue even as the tissue dehydrates or shrinks.

While the sectional view of the jaws 305A and 305B of FIGS. 13–14 depict a preferred embodiment, it should be appreciated that jaws 305A and 305B can use a compressible-resilient PTC matrix 340 in any of the electrode-PTC matrix configurations shown in FIGS. 5–12, all of which fall within the scope of the invention.

5. Type "D" Jaw Structure for Sealing Tissue.

Figure 15:
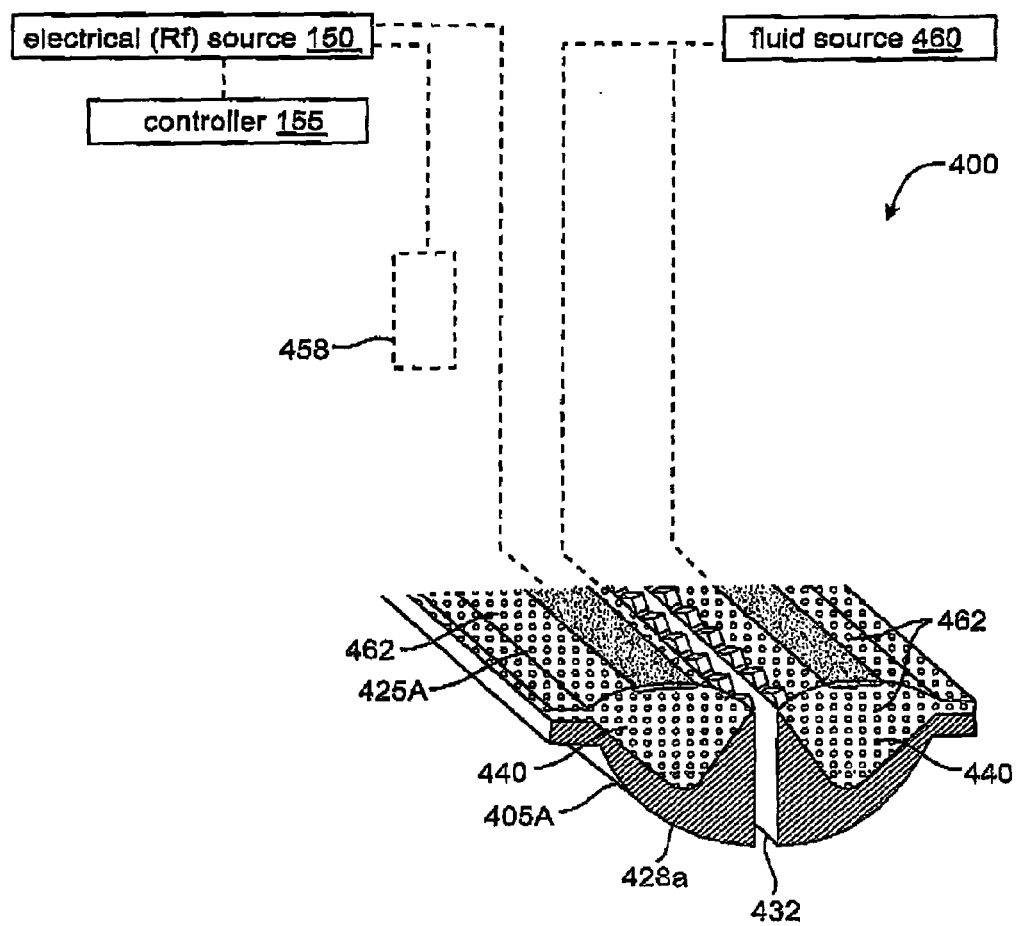
FIG. 15 is a sectional view of a Type "D" jaw in accordance with the invention that has a jaw engagement plane comprising a surface of an open-cell, compressible variably resistive (PTC) material together with a fluid source is coupled thereto for delivering a fluid to the engagement plane.

An exemplary working end of a Type "D" probe 400 is shown in FIG. 15 that again is adapted for energy delivery to an engaged tissue volume for sealing or welding purposes. The jaws 405A and 405B define engagement planes 425A and 425B as described previously that engage tissue from opposing sides. The lower (first) jaw 405A again carries variably resistive portion 440 that is a resilient sponge-type material, e.g., a silicone-based material, that is very similar to that described in the Type "C" embodiment above. The PTC matrix 440 in this embodiment comprises an open cell structure of the silicon polymer or other sponge polymer. More in particular, FIG. 15 illustrates working end 400 with lower (first) jaw 405A defining engagement plane 425A that contacts tissue. The tissue-contacting plane of upper jaw (not shown) can be the same as illustrated in FIG. 14 and comprise an insulator material. Alternatively, the upper jaw can carry electrically conductive body components that match the lower jaw. The jaw structure again is shown in FIG. 15 with a central channel 432 for accommodating a reciprocatable cutting member.

Of particular interest, in the embodiment of FIG. 15, the system is adapted to deliver saline flow from fluid source 460 directly through the open cell structure of the silicon-based PTC conductive layer 460. Such an open cell silicone can be provided adding foaming agents to the silicone during its forming into the shape required for any particular working end. The silicone has a conductive material added to matrix as described above, such as carbon. In this embodiment, an exposed electrode surface 445 comprises an elongate conductive element that exposes portions of the compressible PTC conductive portion 440. Alternatively, the electrode surfaces can be a thin microporous metallic coating, of the types described previously. The electrode 445 is shown as cooperating with a ground pad 458, although any of the electrode and resistive matrix arrangements of FIGS. 5–12 fall within the scope of the invention.

In a method of using the jaw structure of FIG. 15, the system can apply saline solution through pores 462 in the open cell matrix 440 that are exposed in the engagement plane 425A that engages tissue. The method of the invention provides for the infusion of saline during an interval of energy application to engaged tissues to enhance both active Rf heating and conductive heating as the jaws maintain tissue temperature at the selected switching range of the PTC matrix 440. In another aspect of the invention, the compressibility of the silicone-based medial conductive portion 440 can alter the volume and flow of saline within the open cell silicone PTC portion 440. Since the saline is conductive, it functions as a conductor within the cell voids of the medial resistive matrix 440, and plays the exact role as the carbon doping does within the walls of cells that make up the silicone. Thus, the extent of expansion or compression of the silicone medial conductive portion 440 alters its resistivity, wherein the conductive doping of the material remains static. It can be understood that a compression of PTC matrix 440 can collapse the cells or pores 462 which in turn will restrict fluid flow. Thus, the system can be designed with (i) selected conductive doping of silicone PTC matrix 440 and (ii) selected conductivity of the saline solution to optimize the temperature coefficient of the material under different compressed and uncompressed conditions for any particular tissue sealing procedure. The sponge-type variably resistive body portion 440 can be designed to be a positive or negative temperature coefficient material (defined above) as the material expands to a repose shape after being compressed. The resilient engagement surface 425A can naturally expand to remain in substantial contact with the tissue surface as the tissue is sealed and dehydrates and shrinks. At the same time, the cell structure of the medial conductive portion 440 will tend to open to thereby increase fluid flow the engagement plane, which would be desirable to maintain active and passive conductive heating of the tissue. Also at the same time, the selected temperature coefficient of the silicone PTC matrix 440 in combination with the saline volume therein can insure that active Rf heating is modulated as exactly described in the Types "A" and "B" embodiments above with any selected switching range. It is believed that the use of saline inflow will be most useful in welding substantially thin tissue volumes that could otherwise desiccate rapidly during active Rf energy delivery. Thus, this effect can be used to design into the working end certain PTC characteristics to cause the working end to perform in an optimal manner.

It should be appreciated that the scope of the invention includes the use of an open cell elastomer such as silicone to make both a temperature-sensitive variable resistive matrix and a form of pressure-sensitive resistive matrix. As described above, the matrix under compression will collapse pores in the matrix thereby making a conductively-doped elastomer more conductive. In effect, such a matrix can be described as a pressure-sensitive matrix or a combination temperature-sensitive and pressure-sensitive variably resistive matrix. Further, an open cell elastomer that is not conductively-doped can function as a variably resistive matrix in combination with conductive fluid. When under compression, the conductive characteristics of the matrix would be lessened due to the outflow of the conductive fluids. Thus, it can be seen that the variably resistive matrix can be designed in a variety of manners to accomplish various Rf energy delivery objectives, all of which fall within the scope of the invention.

6. Type "E" Jaw Structure for Sealing Tissue

Figure 16:
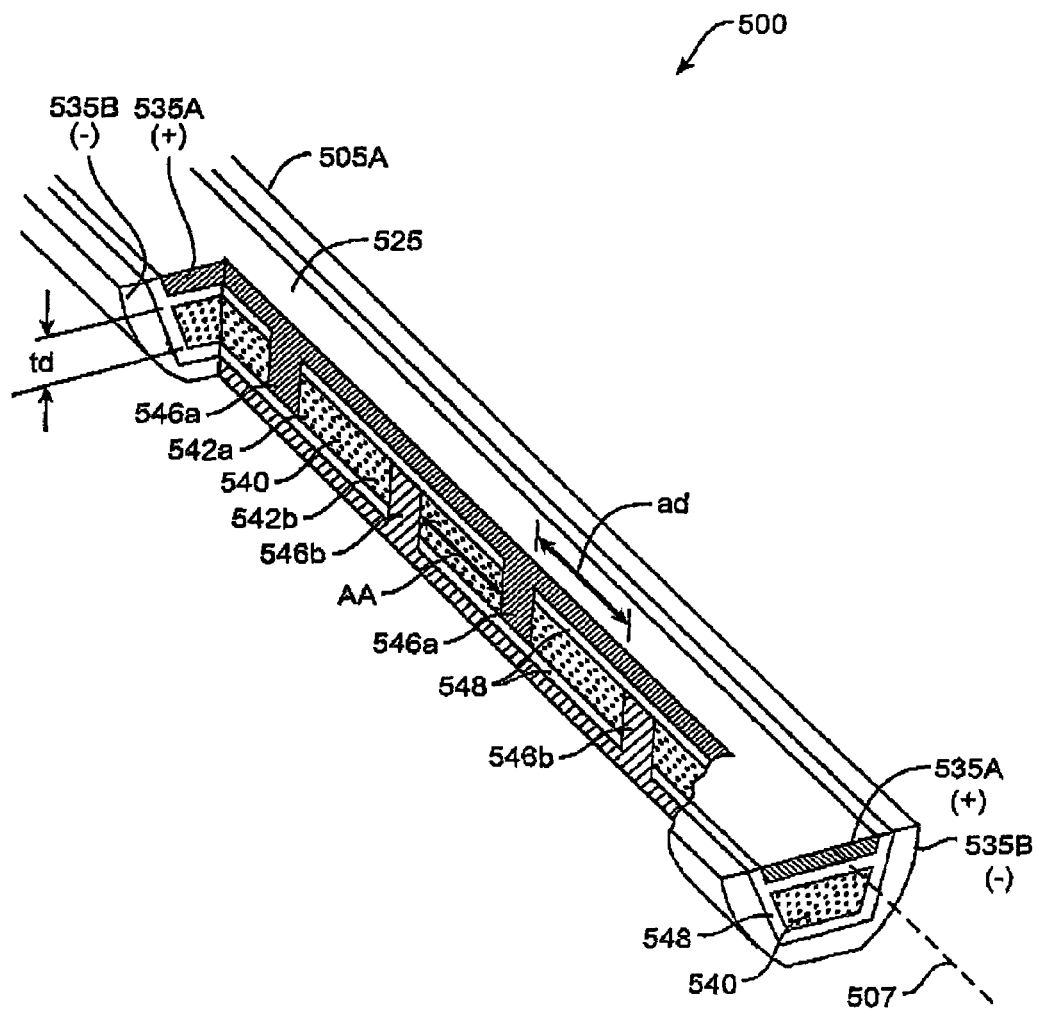
FIG. 16 is a cut-away view of a portion of a Type "E" jaw that carries opposing polarity electrodes with spaced apart volumes of a thermally-sensitive resistive matrix.

An exemplary working end of a Type "E" probe 500 is described with reference to FIG. 16. The Type "E" jaw of FIG. 16 is adapted for controlled energy delivery and is provided with additional features that allows the variably resistive matrix to function optimally in working ends with a small cross-section. The objective to the Type "E" embodiment is to greatly reduce capacitive losses in operation.

In FIG. 16, it can be seen that working end 500 has first jaw 505A (second jaw 505B not shown) that extends along axis 507 with the lower jaw alone carrying the active energy delivery components of the invention, although both jaws could have such active components. The lower jaw 505A defines an engagement plane 525 with cooperating jaw body components that comprise opposing polarity conductive portions 535A and 535B with intermediate elements of a thermally-sensitive resistive matrix indicated at 540. For clarity of explanation, the opposing polarity portions 535A and 535B are indicated as positive (+) and negative (−). The resistive matrix 540 can be any of the types described above and preferably is a rigid ceramic-type positive temperature coefficient (PTC) material (see FIG. 3).

In the Types "A" and "B" working ends of FIGS. 5–9 above, the active jaw carried opposing polarity conductive portions and with an intermediate layer of a variably resistive matrix-which is similar to the Type "E" working end 500. As can be seen, for example in FIG. 6, the transverse dimension td across the variably resistive matrix between the opposing polarity electrodes can be substantially small due to the thin layers of material. The direction of current flow is indicated at A in FIG. 6 which is generally transverse to the axis 107 of the jaws (see FIG. 6).

The Type "E" embodiment of FIG. 16 provides an improved manner of arranging the conductive components of a working end to reduce capacitive coupling of opposing polarity conductive portions 535A and 535B across the variably resistive matrix 540. More in particular, the Type "E" positions elements of the opposing polarity conductive portions 535A and 535B is such a manner to induce a selected directional current flow through the resistive matrix 540, with the preferred direction being any elongated dimension within the jaw structure—typically not a transverse direction across the jaw. The typical preferred direction for inducing current flow is an axial direction in relation to axis 507, with such current flow through matrix indicated at arrow AA in FIG. 16. It should be appreciated that the arrangement of jaw components in FIG. 16 can be provided in jaws that have a channel for receiving a reciprocating blade member as shown in FIGS. 13–14, or combined with any of the electrode configurations of FIGS. 5–12.

In one Type "E" embodiment corresponding to the invention is depicted in FIG. 16, the jaw has at least one volume of resistive matrix 540 that comprises an interior body portion of the jaw (similar to the Type "A" embodiment of FIG. 2). Each said volume of resistive matrix 540 has first and second ends 542a and 542b that contact the respective opposing polarity conductive portions 535A and 535B. The axial dimension ad between the first and second ends 542a and 542b can be any suitable dimension and can be substantially greater than the thickness dimension td of the resistive matrix 540. The conductive portions 535A and 535B each have a projecting leg portion (546a and 546b) that contact the first and second ends 542a and 542b of the resistive matrix 540. As can be seen in FIG. 16, the body portions of the resistive matrix 540, except for the first and second ends 542a–542b thereof, are surrounded by electrically insulative layers indicated at 548. The opposing polarity conductive portions 535A and 535B are coupled to a voltage source. Thus, it can be understood how current is induced to flow in the direction of arrow AA through the matrix 540 to reduce capacitive coupling across the resistive matrix 540. The insulative layer 548 can be any type of material or layer, for example, a thin layer of a titanium oxide ceramic-type material. In another embodiment (not shown), the insulative layer 548 can be an air space. In yet another embodiment, the insulative layer 548 can any combination of air spaces and any other insulative material.

7. Type "F" Jaw Structure for Sealing Tissue

Figure 17:
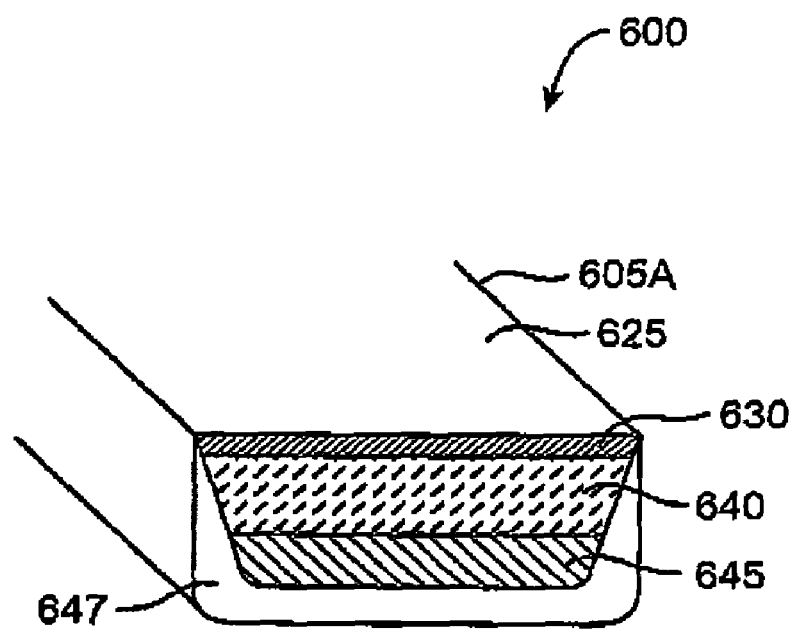
FIG. 17 is a sectional view of a portion of a Type "F" jaw structure that carries variably resistive layer that is pressure sensitive.

FIG. 17 illustrates one jaw of a Type "F" system 600 corresponding to the invention. The jaw structure again is adapted for controlled energy delivery to tissue utilizing a variably resistive matrix 640. The lower jaw 605A defines an engagement plane or surface 625 for contacting tissue that overlies two variably resistive body portions indicated at 630 and 640. The core of the jaw 605A again carries a conductive body portion indicated at 645 that is coupled to a voltage source as described previously. The interior variably resistive matrix 640 is a thermally sensitive material as described in the Types "A" and "B" embodiments, for example, a PTC matrix of a ceramic material. An optional structural body of the jaws is indicated at 647 which is insulated from the above-described electrically active components.

Of particular interest, the exterior variably resistive matrix 630 is of a pressure-sensitive resistive material that is carried across the engagement plane 625. In one embodiment, such a variably resistive layer 630 can be substantially thin and fabricated of a material described as a "pressure variable resistor ink" and is more specifically identified as Product No. CMI 118-44 available from Creative Materials Inc., 141 Middlesex Rd., Tyngsboro, Mass. 01879. The resistance vs. pressure characteristics of the pressure-sensitive resistive matrix 630 can be adjusted by blending the above-described material with Product No. CMI 117-34 that is available from the same source.

In operation, it can be understood that any pressure against the pressure-sensitive resistive layer 630 will locally decrease its resistance to current flow therethrough. As the jaws are closed, the engagement plane 625 of the lower jaw 605A will be pressed against the tissue. Due to the potential pressure vs. resistivity characteristics of the resistive layer 630, the layer can be designed so that Rf current will only flow through localized portions of the engagement plane 625 where the pressure-sensitive resistive layer 830 is under substantial pressure, which in turn locally lowers the resistance of a portion of the surface layer. Further, the interior thermally-sensitive variable sensitive resistive layer 640 will modulate Rf flow as previously described to maintain a targeted tissue temperature.

It should be appreciated that the scope of the invention and its method of use of the includes the use of jaw working surface similar to that of FIG. 17 that does not carry an interior body portion of the thermally-sensitive resistive matrix indicated at 640. In other words, the jaw can rely only on the pressure-sensitive resistive layer 630 about the engagement plane 625 to locally apply energy to captures tissue volumes.

In another embodiment (not shown), either one both jaws can have an elongate core of the substantially resistive material in addition to the core electrode and a variably resistive matrix of any type described above. The resistive material has a fixed resistance and is adapted to pre-heat the jaw, its engagement plane and the engaged tissue as a means of pre-conditioning the tissue to attain a certain selected impedance. Such a system will be useful when the engagement plane is large in dimension. A thermally conductive, but electrically insulative, layer can be disposed intermediate the fixed resistance material and a conductive (electrode) layer. The conductive layer is coupled in series with the fixed resistance material to the remote voltage source. The variably resistive matrix is disposed between the engagement plane and the conductive (electrode) layer—as described in any of the Types "A" and "B" embodiments above.

Those skilled in the art will appreciate that the exemplary systems, combinations and descriptions are merely illustrative of the invention as a whole, and that variations of components, dimensions, and compositions described above may be made within the spirit and scope of the invention. Specific characteristics and features of the invention and its method are described in relation to some figures and not in others, and this is for convenience only. While the principles of the invention have been made clear in the exemplary descriptions and combinations, it will be obvious to those skilled in the art that modifications may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

What is claimed is:

1. A working end of a surgical instrument for delivering energy to tissue, comprising:
  paired first and second jaw members moveable between an open position and a closed position; and
  at least one jaw including an electrode, a first body portion comprising an electrically conductive material having a temperature-sensitive variable resistance which increases with an increase in the temperature of the material for responding to the temperature of the tissue, and a second body portion comprising a conductive material, the second portion configured to be coupled to an Rf voltage source, the electrode and the second body portion configured to be coupled to separate poles of the Rf voltage source, wherein the first body portion is disposed between the second body portion and the electrode to control the passage of electrical current from the second body portion to the electrode and wherein said at least one jaw defines a surface engagement plane for engaging tissue, said engagement plane carrying an exposed surface of said first body portion.

2. The working end of claim 1, said engagement plane carrying an exposed surface of said second body portion.

3. The working end of claim 1, wherein said first body portion comprises a ceramic composition.

4. The working end of claim 1, wherein said first body portion defines a switching range at which its electrical resistance substantially varies in a selected temperature range.

5. The working end of claim 4, wherein said switching range falls between about 40° C. and 200° C.

6. A working end of a surgical instrument for delivering energy to tissue, comprising:
paired first and second jaw members moveable between an open position and a closed position; and
at least one jaw including an electrode adapted for contacting tissue, a first body portion comprising an electrically conductive material having a temperature-sensitive variable resistance which increases with an increase in the temperature of the material for responding to the temperature of the tissue, and a second body portion comprising a conductive material, the second portion configured to be coupled to an Rf voltage source, the electrode and the second body portion configured to be coupled to separate poles of the Rf voltage source, wherein the first body portion is disposed between the second body portion and to electrode to control the passage of electrical current from to second body portion to the electrode responsive to the temperature of contacted tissue and wherein said at least one jaw defines a surface engagement plane for engaging tissue, said engagement plane carrying an exposed surface of said first body portion.

7. The working end of claim 6, said engagement plane carrying an exposed surface of said second body portion.

8. The working end of claim 7, wherein said first body portion comprises a ceramic composition.

9. The working end of claim 6, wherein said first body portion defines a switching range at which its electrical resistance substantially increases or decreases in a selected temperature range.

10. The working end of claim 9, wherein said switching range falls between about 40° C. and 200° C.

* * * * *

UNITED STATES PATENT AND TRADEMARK OFFICE
CERTIFICATE OF CORRECTION

| | |
|---|---|
| PATENT NO. | : 7,186,253 B2 |
| APPLICATION NO. | : 11/118881 |
| DATED | : March 6, 2007 |
| INVENTOR(S) | : Csaba Truckai et al. |

It is certified that error appears in the above-identified patent and that said Letters Patent is hereby corrected as shown below:

Claim 6, Column 17, Line 16: Replace the word "to" with the word "the".

Claim 6, Column 17, Line 17: Replace the last occurrence of the word "to" with the word "the".

Signed and Sealed this
Twelfth Day of July, 2011

David J. Kappos
*Director of the United States Patent and Trademark Office*